(12) United States Patent
Scott et al.

(10) Patent No.: US 10,329,291 B2
(45) Date of Patent: Jun. 25, 2019

(54) C5-C6-CARBOCYCLIC FUSED IMINOTHIADIAZINE DIOXIDES AS BACE INHIBITORS, COMPOSITIONS, AND THEIR USE

(71) Applicant: Merck Sharp & Dohme Corp., Rahway, NJ (US)

(72) Inventors: Jack D. Scott, Scotch Plains, NJ (US); Timothy A. Blizzard, Princeton, NJ (US); Shawn P. Walsh, Bridgewater, NJ (US); Jared N. Cumming, Winchester, MA (US)

(73) Assignee: Merck Sharp & Dohme Corp.

( * ) Notice: Subject to any disclaimer, the term of this patent is extended or adjusted under 35 U.S.C. 154(b) by 0 days.

(21) Appl. No.: 15/780,651

(22) PCT Filed: Nov. 29, 2016

(86) PCT No.: PCT/US2016/063892
§ 371 (c)(1),
(2) Date: Jun. 1, 2018

(87) PCT Pub. No.: WO2017/095759
PCT Pub. Date: Jun. 8, 2017

(65) Prior Publication Data
US 2018/0354943 A1 Dec. 13, 2018

Related U.S. Application Data

(60) Provisional application No. 62/263,046, filed on Dec. 4, 2015.

(51) Int. Cl.
| | |
|---|---|
| *C07D 471/04* | (2006.01) |
| *C07D 417/12* | (2006.01) |
| *C07D 285/20* | (2006.01) |
| *A61P 25/28* | (2006.01) |

(52) U.S. Cl.
CPC ............ *C07D 471/04* (2013.01); *A61P 25/28* (2018.01); *C07D 285/20* (2013.01); *C07D 417/12* (2013.01)

(58) Field of Classification Search
CPC .. C07D 471/04; C07D 417/12; C07D 285/20; A61P 25/28
See application file for complete search history.

(56) References Cited

U.S. PATENT DOCUMENTS

| | | | |
|---|---|---|---|
| 8,183,252 B2 | 5/2012 | Zhu et al. | |
| 8,557,826 B2 | 10/2013 | Stamford et al. | |
| 8,563,543 B2 | 10/2013 | Scott et al. | |
| 8,569,310 B2 | 10/2013 | Iserloh et al. | |
| 8,729,071 B2 | 5/2014 | Scott et al. | |
| 8,946,210 B2 | 2/2015 | Suzuki et al. | |
| 9,145,426 B2 | 9/2015 | Stamford et al. | |
| 9,181,236 B2 | 11/2015 | Wu et al. | |
| 9,221,839 B2 | 12/2015 | Cumming et al. | |
| 9,365,589 B2 | 6/2016 | Cumming et al. | |
| 9,416,129 B2 | 8/2016 | Gilbert et al. | |
| 9,422,255 B2 | 8/2016 | Khan et al. | |
| 9,422,277 B2 | 8/2016 | Gilbert et al. | |
| 9,428,476 B2 | 8/2016 | Khan et al. | |
| 9,447,085 B2 | 9/2016 | Cumming et al. | |
| 9,453,034 B2 | 9/2016 | Gilbert et al. | |
| 9,489,013 B2 | 11/2016 | Cumming et al. | |
| 9,499,502 B2 | 11/2016 | Wu et al. | |
| 9,580,396 B2 | 2/2017 | Cumming et al. | |
| 9,868,738 B2 | 1/2018 | Liu et al. | |
| 9,957,269 B2 | 5/2018 | Cumming et al. | |
| 2014/0023667 A1 | 1/2014 | Stamford et al. | |
| 2014/0023668 A1* | 1/2014 | Cumming ............ | C07D 513/04 424/184.1 |

(Continued)

FOREIGN PATENT DOCUMENTS

| | | |
|---|---|---|
| WO | 2014099788 A1 | 6/2014 |
| WO | 2015038446 A1 | 3/2015 |

OTHER PUBLICATIONS

International Search Report for PCT/US16/063892 dated Feb. 15, 2017, 8 pages.

*Primary Examiner* — Niloofar Rahmani
(74) *Attorney, Agent, or Firm* — Catherine D. Fitch; Keith D. MacMillan

(57) ABSTRACT

In its many embodiments, the present invention provides certain C5-C6-carbocyclic fused iminothiazine dioxide compounds, including compounds Formula (I): and tautomers thereof, and pharmaceutically acceptable salts of said compounds and said tautomers, wherein $R^1$, ring A, $R^4$, m, -$L_1$-, ring B, $R^B$, n, q, ring C, $R^C$, and p are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

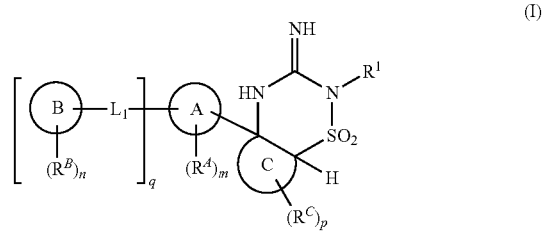

(I)

14 Claims, No Drawings

(56) References Cited

U.S. PATENT DOCUMENTS

| | | |
|---|---|---|
| 2016/0222032 A1 | 8/2016 | Scott et al. |
| 2016/0326155 A1 | 11/2016 | Scott et al. |
| 2017/0037056 A1 | 2/2017 | Dai et al. |
| 2017/0114065 A1 | 4/2017 | Walsh et al. |
| 2017/0233383 A1 | 8/2017 | Trzaska et al. |
| 2017/0246300 A1 | 8/2017 | He et al. |
| 2017/0362248 A1 | 12/2017 | Dai et al. |
| 2017/0369484 A1 | 12/2017 | Wu et al. |

* cited by examiner

C5-C6-CARBOCYCLIC FUSED IMINOTHIADIAZINE DIOXIDES AS BACE INHIBITORS, COMPOSITIONS, AND THEIR USE

FIELD OF THE INVENTION

This invention provides certain C5-C6-carbocyclic fused iminothidiazine dioxide compounds, and compositions comprising these compounds, as inhibitors of BACE, which may be useful for treating or preventing pathologies related thereto.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5×FAD mice abrogates Aβ generation, blocks amyloid deposition, prevents neuron loss found in the cerebral cortex and subiculum (brain regions manifesting the most severe amyloidosis in 5×FAD mice), and rescues memory deficits in 5×FAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE-1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009; Yu, et al., "Lithium reduces BACE1 overexpression, β amyloid accumulation, and spatial learning deficits in mice with traumatic brain injury", J Neurotrauma, 2012 September; 29(13):2342-51; Tran, et al., "Controlled cortical impact traumatic brain injury in 3×Tg-AD mice causes acute intra-axonal amyloid-β accumulation and independently accelerates the development of tau abnormalities", J Neurosci. 2011 Jun. 29; 31(26):9513-25.) Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

SUMMARY OF THE INVENTION

The present invention provides certain C5-C6-carbocyclic fused iminothidiazine dioxide compounds, which are collectively or individually referred to herein as "compound(s) of the invention", as described herein. The compounds of the invention are inhibitors of BACE-1 and/or BACE-2, and may be useful for treating or preventing diseases or pathologies related thereto.

In one embodiment, the compounds of the invention have the structural Formula (I):

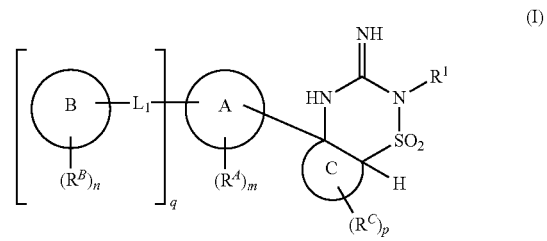

or a tautomer thereof having the structural Formula (I'):

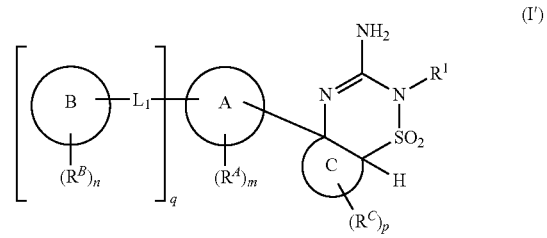

or pharmaceutically acceptable salt thereof, wherein:

ring C is a 3-, 4-, 5-, or 6-membered fused cycloalkyl group;

p is 1, 2, 3, or 4, provided that the value of p does not exceed the number of substitutable hydrogen atoms on ring C;

each $R^C$ is independently selected from the group consisting of H, F, —OH, oxo, lower alkyl, lower cycloalkyl, —O-(lower alkyl) and —O-(lower cycloalkyl),
  wherein each said lower alkyl and lower cycloalkyl are optionally substituted with one or more fluorine, and
  wherein 1 to 2 non-adjacent, non-terminal carbon atoms in each said lower alkyl are optionally independently replaced with —O—, —NH—, —N-(lower alkyl)-, —S—, —S(O)—, or —S(O)$_2$—;

$R^1$ is selected from the group consisting of H, lower alkyl, lower cycloalkyl, and -(lower alkyl)-(lower cycloalkyl),
  wherein each said lower alkyl and lower cycloalkyl are optionally substituted with one or more fluorine, and
  wherein 1 to 2 non-adjacent, non-terminal carbon atoms in each said lower alkyl are optionally independently replaced with —O—, —NH—, —N-(lower alkyl)-, —S—, —S(O)—, or —S(O)$_2$—;

ring A is selected from the group consisting of aryl and heteroaryl;

m is 0, 1, 2, or 3, provided that the value of m does not exceed the number of substitutable hydrogen atoms on ring A;

each $R^A$ (when present) is independently selected from the group consisting of halogen, —CN, —OH, oxo, —NH-(lower alkyl), —NHC(O)-(lower alkyl), lower alkyl, -(lower alkyl)-(lower cycloalkyl), and —O-(lower alkyl),
  wherein each said lower alkyl and lower cycloalkyl are optionally substituted with one or more fluorine, and
  wherein 1 to 2 non-adjacent, non-terminal carbon atoms in each said lower alkyl are optionally independently replaced with —O—, —NH—, —N-(lower alkyl), —S—, —S(O)—, or —S(O)$_2$—;

q is 0 or 1;

-L$_1$-, when present, represents a bond or a divalent moiety selected from the group consisting of —C(O)NH—, —CH$_2$C(O)NH—, —NH—, —CH(CH$_3$)NH—, —CH$_2$NH—, —O—, and —CH$_2$O—;

ring B, when present, is selected from the group consisting of aryl, heteroaryl, cycloalkyl, and heterocycloalkyl;

n is 0, 1, 2, or 3, provided that the value of n does not exceed the number of substitutable hydrogen atoms on ring B; and each $R^B$, when present, is independently selected from the group consisting of halogen, —CN, —OH, oxo, lower alkyl, lower cycloalkyl, -(lower alkyl)-(lower cycloalkyl), —O-(lower alkyl), —O-(lower cycloalkyl), —O-(lower alkyl)-(lower cycloalkyl), —C≡CH, —C≡C—CH$_3$, —OCH$_2$—C≡C—H, and —OCH$_2$—C≡C—CH$_3$,
  wherein each said lower alkyl and lower cycloalkyl are optionally substituted with one or more fluorine, and
  wherein 1 to 2 non-adjacent, non-terminal carbon atoms in each said lower alkyl are optionally independently replaced with —O—, —NH—, —N-(lower alkyl)-, —S—, —S(O)—, or —S(O)$_2$—.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formulas (I) or (I'). In each of the embodiments described herein, each variable is selected independently of the other unless otherwise noted.

As "oxo" is a divalent moiety, it shall be understood that, in each of Formulas (I), (I'), (IA), (IA'), (II), (II'), (IIA), (IIA'), (III), (III'), (IIIA), (IIIA'), (IV), (IV'), (IVA), and (IVA'), when $R^C$ is oxo, each hydrogen bound to the ring carbon atom to which $R^C$ is shown attached is replaced with =$R^C$, as shown in the following non-limiting examples:

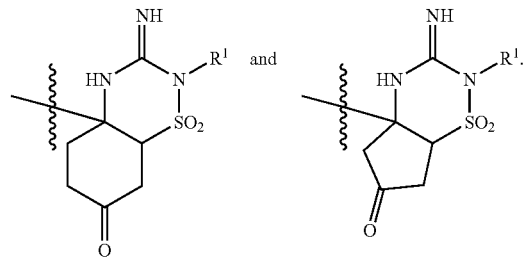

In one embodiment, the compounds of the invention have the structural Formula (I) above.

In another embodiment, the compounds of the invention have the structural Formula (IA):

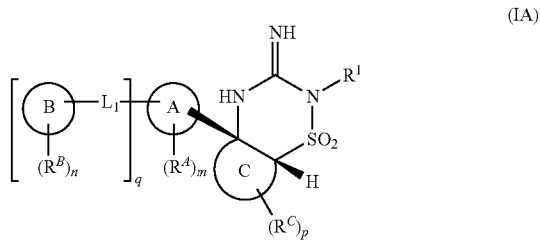

(IA)

or a tautomer thereof having the structural Formula (IA'):

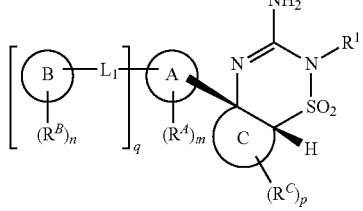
(IA')

or pharmaceutically acceptable salt thereof, wherein each variable is as defined in Formula (I).

In another embodiment, in each of Formulas (I), (I'), (IA), and (IA'):

p is 1 or 2, provided that the value of p does does not exceed total number of valences on ring C; and each $R^C$ is independently selected from the group consisting of H, F, —OCH₃, and oxo.

In an alternative of the immediately preceding embodiment, p is 2. In another alternative of the immediately preceeding embodiment, p is 1.

In another embodiment, the compounds of the invention have the structural Formula (II):

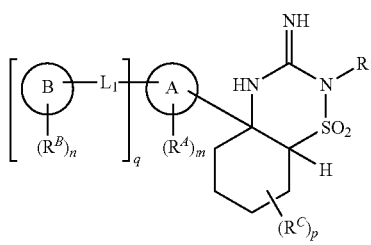
(II)

or a tautomer thereof having the structural Formula (II'):

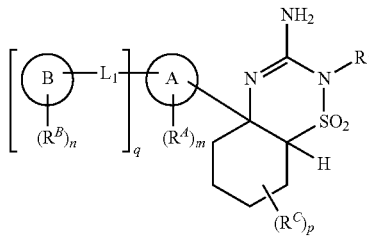
(II')

or a pharmaceutically acceptable salt thereof, wherein each variable is as defined in Formula (I).

In another embodiment, the compounds of the invention have the structural Formula (IIA):

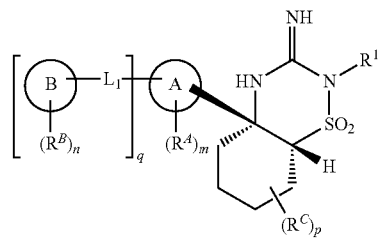
(IIA)

or a tautomer thereof having the structural Formula (IIA'):

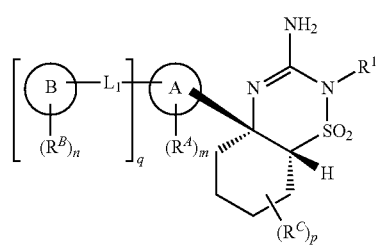
(IIA')

or a pharmaceutically acceptable salt thereof, wherein each variable is as defined in Formula (I).

In another embodiment, in each of Formulas (II), (II'), (IIA), and (IIA'):

p is 1 or 2; and each $R^C$ is independently selected from the group consisting of H, F, —OCH₃, and oxo.

In an alternative of the immediately preceding embodiment, p is 2. In another alternative of the immediately preceeding embodiment, p is 1.

In an another alternative of the immediately preceding embodiment, p is 2;

ring C is

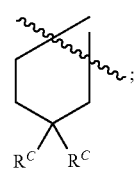

and
each $R^C$ is F.

In another alternative of the immediately preceeding embodiment, p is 1;
ring C is

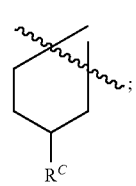

and
$R^C$ is selected from the group consisting of H, F, —OCH₃, and oxo.

In another embodiment, the compounds of the invention have the structural Formula (III):

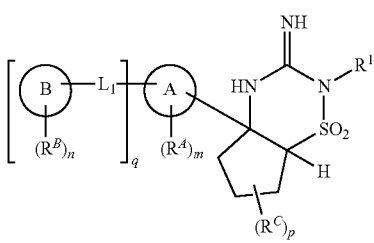

(III)

or a tautomer thereof having the structural Formula (III'):

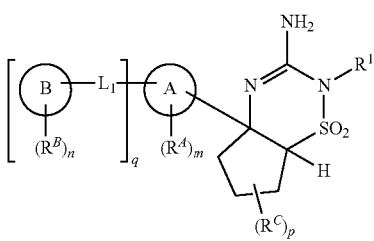

(III')

or a pharmaceutically acceptable salt thereof, wherein each variable is as defined in Formula (I).

In another embodiment, the compounds of the invention have the structural Formula (IIIA):

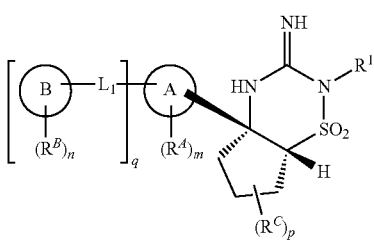

(IIIA)

or a tautomer thereof having the structural Formula (IIIA'):

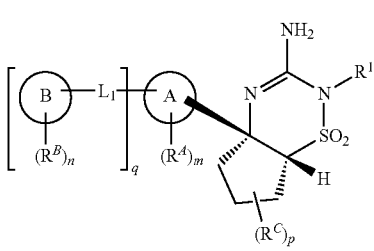

(IIIA')

or a pharmaceutically acceptable salt thereof, wherein each variable is as defined in Formula (I).

In another embodiment, in each of Formulas (III), (III'), (IIIA), and (IIIA'):

p is 1 or 2; and each $R^C$ is independently selected from the group consisting of H, F, —OCH$_3$, and oxo.

In an alternative of the immediately preceding embodiment, p is 2. In another alternative of the immediately preceeding embodiment, p is 1.

In an another alternative of the immediately preceding embodiment, p is 2;

ring C is

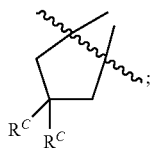

and each $R^C$ is F.

In another alternative of the immediately preceeding embodiment, p is 1;

ring C is

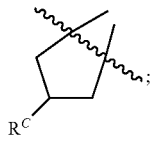

and $R^C$ is selected from the group consisting of H, F, —OCH$_3$, and oxo.

In another embodiment, the compounds of the invention have the structural Formula (IV):

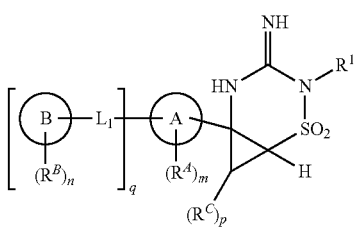

(IV)

or a tautomer thereof having the structural Formula (IV'):

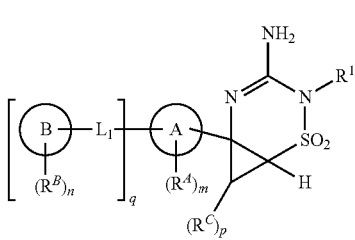

(IV')

or a pharmaceutically acceptable salt thereof, wherein each variable is as defined in Formula (I).

In another embodiment, the compounds of the invention have the structural Formula (IVA):

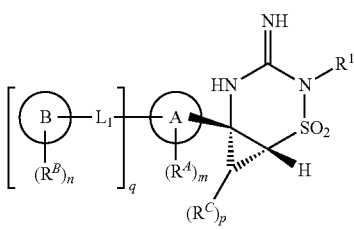

or a tautomer thereof having the structural Formula (IVA'):

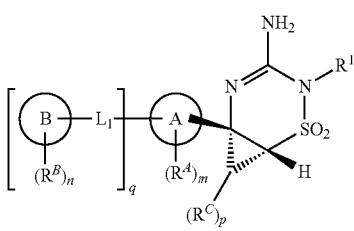

or a pharmaceutically acceptable salt thereof, wherein each variable is as defined in Formula (I).

In another embodiment, in each of Formulas (IV), (IV'), (IVA), and (IVA'):

p is 1 or 2; and each $R^C$ is independently selected from the group consisting of H, F, and —$OCH_3$.

In an alternative of the immediately preceding embodiment, p is 2. In another alternative of the immediately preceeding embodiment, p is 1.

In an another alternative of the immediately preceding embodiment, p is 2;
ring C is

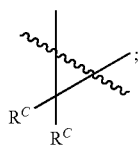

and
each $R^C$ is F.

In another alternative of the immediately preceeding embodiment, p is 1;
ring C is

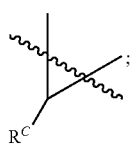

and
$R^C$ is selected from the group consisting of H, F, and —$OCH_3$.

The following alternative embodiments of $R^1$ are applicable to each of the embodiments described hereinabove.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

$R^1$ is selected from the group consisting of H, methyl, ethyl, cyclopropyl, —$CH_2$-cyclopropyl, and —$CH_2CH_2OCH_3$.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

$R^1$ is selected from the group consisting of H and methyl.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

$R^1$ is methyl.

In some embodiments, in each of Formulas (I), (I'), (IA), (IA'), (II), (II'), (IIA), (IIA'), (III), (III'), (IIIA), (IIIA'), (IV), (IV'), (IVA), and (IVA'), q is 1. In these embodiments, the moiety:

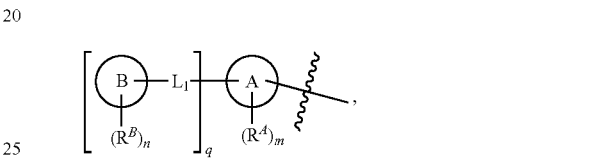

has the form:

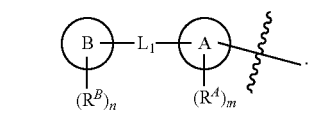

The following alternative embodiments of q and -$L_1$- are applicable to each of the embodiments described hereinabove.

In one embodiment, in each of Formulas (I), (I'), (IA), (IA'), (II), (II'), (IIA), (IIA'), (III), (III'), (IIIA), (IIIA'), (IV), (IV'), (IVA), and (IVA'):

q=1; and -$L_1$- is selected from the group consisting of —C(O)NH—, —NH—, and —O—.

In one embodiment, in each of Formulas (I), (I'), (IA), (IA'), (II), (II'), (IIA), (IIA'), (III), (III'), (IIIA), (IIIA'), (IV), (IV'), (IVA), and (IVA'):

q=1; and -$L_1$- is a bond.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1; and -$L_1$- is —C(O)NH—.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1; and -$L_1$- is —NH—.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1; and -$L_1$- is —$CH_2$C(O)NH—.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1; and -$L_1$- is —CH($CH_3$)NH—.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1; and -$L_1$- is —$CH_2$NH—.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1; and -$L_1$- is —O—.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1; and -$L_1$- is —$CH_2O$—.

The following alternative embodiments of ring A, $R^A$, and m are applicable to each of the embodiments described hereinabove.

In one embodiment, in each of Formulas (I), (I'), (IA), (IA'), (II), (II'), (IIA), (IIA'), (III), (III'), (IIIA), (IIIA'), (IV), (IV'), (IVA), and (IVA'):

q=1;

ring A is selected from the group consisting of phenyl, pyridazinyl, pyridinyl, pyrimidinyl, pyrazinyl, pyrazolyl, triazinyl, thiazolyl, and thienyl;

m is 0, 1, 2, or 3, provided that the value of m does not exceed the number of available substitutable hydrogen atoms on ring A; and each $R^A$ (when present) is independently selected from the group consisting of fluoro, chloro, bromo, —CN, methyl, ethyl, cyclopropyl, —$CH_2OCH_3$, —$CF_3$, —$CHF_2$, —$CH_2F$, —$OCH_3$, —$OCF_3$, and —$OCHF_2$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

ring A is selected from the group consisting of phenyl and pyridinyl;

m is 0, 1, 2, or 3; and each $R^A$, when present, is independently selected from the group consisting of fluoro, chloro, methyl, and —$CHF_2$.

In an alternative of the immediately embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), (IA'), (II), (II'), (IIA), (IIA'), (III), (III'), (IIIA), (IIIA'), (IV), (IV'), (IVA), and (IVA');

q=1;

ring A is selected from the group consisting of phenyl and pyridinyl;

m is 0, 1, 2, or 3; and each $R^A$, when present, is fluoro.

In an alternative of the immediately preceding embodiment, m is 0. In another alternative of the immediately preceding embodiment, m is 1. In another alternative of the immediately preceding embodiment, m is 2.

The following alternative embodiments of ring B, $R^B$ and n are contemplated in combination with each of the embodiments described hereinabove.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-$L_1$- is —C(O)NH—;

ring B is selected from the group consisting of phenyl, pyridinyl, pyrazinyl, pyrimidinyl, and pyridazinyl;

n is 0, 1, 2, or 3; and each $R^B$, when present, is independently selected from the group consisting of fluoro, chloro, bromo, —CN, —OH, methyl, ethyl, cyclopropyl, —$CH_2OCH_3$, —C≡CH, —C≡C—$CH_3$, —$CF_3$, —$CHF_2$, —$CH_2F$, —$OCH_2$—C≡C—H, —$OCH_2$—C≡C—$CH_3$, —$OCH_3$, —$OCF_3$, —$OCHF_2$, —$OCH_2F$, —$OCH_2CF_3$, —$OCH_2CHF_2$, and —$OCH_2CH_2F$.

In an alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-$L_1$- is —C(O)NH—;

ring B is selected from the group consisting of pyridinyl and pyrazinyl;

n is 0, 1, 2, or 3; and each $R^B$ (when present) is independently selected from the group consisting of fluoro, chloro, —CN, methyl, —$CF_3$, —$OCH_2$—C≡C—H, —$OCH_3$, —$OCHF_2$, —$OCH_2CF_3$, and —$OCH_2CH_2F$.

In an alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-$L_1$- is —C(O)NH—;

ring A is selected from the group consisting of phenyl and pyridinyl;

m is 0, 1, 2, or 3;

each $R^A$, when present, is independently selected from the group consisting of fluoro, chloro, methyl, and —$CHF_2$.

ring B is selected from the group consisting of phenyl, pyridinyl, pyrazinyl, pyrimidinyl, and pyridazinyl;

n is 0, 1, 2, or 3; and each $R^B$ (when present) is independently selected from the group consisting of fluoro, chloro, bromo, —CN, —OH, methyl, ethyl, cyclopropyl, —$CH_2OCH_3$, —C≡CH, —C≡C=$CH_3$, —$CF_3$, —$CHF_2$, —$CH_2F$, —$OCH_2$—C≡C—H, —$OCH_2$—C≡C—$CH_3$, —$OCH_3$, —$OCF_3$, —$OCHF_2$, —$OCH_2F$, —$OCH_2CF_3$, —$OCH_2CHF_2$, and —$OCH_2CH_2F$.

In an alternative of the immediately embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-$L_1$- is —C(O)NH—;

ring A is selected from the group consisting of phenyl and pyridinyl;

m is 0, 1, 2, or 3;

each $R^A$ (when present) is fluoro;

ring B is selected from the group consisting of pyridinyl and pyrazinyl;

n is 0, 1, 2, or 3; and each $R^B$ (when present) is independently selected from the group consisting of fluoro, chloro, —CN, methyl, —CF$_3$, —OCH$_2$—C≡C—H, —OCH$_3$, —OCHF$_2$, —OCH$_2$CF$_3$, and —OCH$_2$CH$_2$F.

In an alternative of the immediately preceding embodiment, m is 0. In another alternative of the immediately preceding embodiment, m is 1. In another alternative of the immediately preceding embodiment, m is 2.

In another alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-L$_1$- is —NH—;

ring B is selected from the group consisting of benzimidazolyl, benzoisothiazolyl, benzoisoxazolyl, benzothiazolyl, benzoxazolyl, dihydrocyclopentapyridinyl, dihydroindenyl, imidazopyrazinyl, imidazopyridinyl, imidazopyrimidinyl, imidazothiazolyl, indenyl, indolyl, isoquinolinyl, naphthyridinyl, phenyl, phthalazinyl, pteridinyl, pyrazinopyridazinyl, pyrazinyl, pyrazolopyridinyl, pyrazolopyrimidinyl, pyridinyl, pyridazinyl, pyridopyrazinyl, pyridopyridazinyl, pyridopyrimidinyl, pyrimidinyl, pyrrolopyridinyl, pyrrolopyrimidinyl, quinazolinyl, quinolinyl, quinoxalinyl, tetrahydroisoquinolinyl, tetrahydroquinolinyl, and thienylpyridinyl;

n is 0, 1, 2, or 3; and each $R^B$ (when present) is independently selected from the group consisting of fluoro, chloro, bromo, —CN, —OH, methyl, ethyl, cyclopropyl, —CH$_2$OCH$_3$, —C≡CH, —C≡C—CH$_3$, —CF$_3$, —CHF$_2$, —CH$_2$F, —OCH$_2$—C≡C—H, —OCH$_2$—C≡C—CH$_3$, —OCH$_3$, —OCF$_3$, —OCHF$_2$, —OCH$_2$F, —OCH$_2$CF$_3$, —OCH$_2$CHF$_2$, and —OCH$_2$CH$_2$F.

In an alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-L$_1$- is —NH—;

ring B is selected from the group consisting of pyridinyl, pyrazinyl, dihydrocyclopentapyridinyl, dihydroindenyl, naphthyridinyl, pteridinyl, pyridopyrazinyl, pyridopyrimidinyl, and tetrahydroquinolinyl;

n is 0, 1, 2, or 3; and each $R^B$ (when present) is independently selected from the group consisting of fluoro, chloro, bromo, —CN, —CF$_3$, —CHF$_2$, —OCH$_3$, —OCF$_3$, —OCHF$_2$, —OCH$_2$CF$_3$, and —OCH$_2$CHF$_2$.

In an alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-L$_1$- is —NH—;

ring B is selected from the group consisting of naphthyridinyl, pyridopyrazinyl, and pyridopyrimidinyl;

n is 0, 1, 2, or 3; and each $R^B$ (when present) is independently selected from the group consisting of fluoro, bromo, —CN, —CF$_3$, and —OCH$_3$.

In an alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-L$_1$- is —NH—;

ring A is selected from the group consisting of phenyl and pyridinyl;

m is 0, 1, 2, or 3;

each $R^A$ (when present) is independently selected from the group consisting of fluoro, chloro, methyl, and —CHF$_2$;

ring B is selected from the group consisting of pyridinyl, pyrazinyl, dihydrocyclopentapyridinyl, dihydroindenyl, naphthyridinyl, pteridinyl, pyridopyrazinyl, pyridopyrimidinyl, and tetrahydroquinolinyl;

n is 0, 1, 2, or 3; and each $R^B$ (when present) is independently selected from the group consisting of fluoro, chloro, bromo, —CN, —CF$_3$, —CHF$_2$, —OCH$_3$, —OCF$_3$, —OCHF$_2$, —OCH$_2$CF$_3$, and —OCH$_2$CHF$_2$.

In an alternative of the immediately preceding embodiment, m is 0. In another alternative of the immediately preceding embodiment, m is 1. In another alternative of the immediately preceding embodiment, m is 2.

In another alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-L$_1$- is —NH—;

ring A is selected from the group consisting of phenyl and pyridinyl;

m is 0, 1, 2, or 3;

each $R^A$ (when present) is fluoro;

ring B is selected from the group consisting of naphthyridinyl, pyridopyrazinyl, and pyridopyrimidinyl;

n is 0, 1, 2, or 3; and each $R^B$ (when present) is independently selected from the group consisting of fluoro, bromo, —CN, —CF$_3$, and —OCH$_3$.

In an alternative of the immediately preceding embodiment, m is 0. In another alternative of the immediately preceding embodiment, m is 1. In another alternative of the immediately preceding embodiment, m is 2.

In another alternative of the immediately preceeding embodiment, n is 0. In another alternative of the immediately preceeding embodiment, n is 1. In another alternative of the immediately preceeding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;

-L$_1$- is —O—;

ring B is selected from the group consisting of cyclobutyl, cyclohexyl, cyclopentyl, phenyl, pyrazinyl, pyridazinyl, pyridinyl, pyrimidinyl, and tetrahydropyranyl;

n is 0, 1, or 2; and each $R^B$ group (when present) is independently selected from the group consisting of fluoro, chloro, bromo, —CN, methyl, cyclopropyl, —CH$_2$OCH$_3$, —C≡CH, —C≡C—CH$_3$, —CF$_3$, —CHF$_2$, —CH$_2$F, —OCH$_2$—C≡C—H, —OCH$_2$—C≡C—CH$_3$, —OCH$_3$, —OCF$_3$, —OCHF$_2$, —OCH$_2$F, —OCH$_2$CF$_3$, —OCH$_2$CHF$_2$, and —OCH$_2$CH$_2$F.

In an alternative of the immediately preceding embodiment, n is 0. In another alternative of the immediately preceding embodiment, n is 1. In another alternative of the immediately preceding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;
-L$_1$- is —O—;
ring B is selected from the group consisting of pyrazinyl, pyridinyl, and pyrimidinyl;
n is 0, 1, or 2; and
each $R^B$ group (when present) is independently selected from the group consisting of fluoro, —CN, —CF$_3$ and —OMe.

In an alternative of the immediately preceding embodiment, n is 0. In another alternative of the immediately preceding embodiment, n is 1. In another alternative of the immediately preceding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;
-L$_1$- is —O—;
ring B is pyridinyl;
n is 0, 1, or 2; and
$R^B$ (when present) is fluoro.

In an alternative of the immediately preceding embodiment, n is 0. In another alternative of the immediately preceding embodiment, n is 1. In another alternative of the immediately preceding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;
-L$_1$- is —O—;
ring A is selected from the group consisting of phenyl and pyridinyl;
m is 0, 1, 2, or 3;
each $R^A$ (when present) is independently selected from the group consisting of fluoro, chloro, methyl, and —CHF$_2$;
ring B is selected from the group consisting of pyrazinyl, pyridinyl, and pyrimidinyl;
n is 0, 1, or 2; and
each $R^B$ group (when present) is independently selected from the group consisting of fluoro, —CN, —CF$_3$ and —OMe.

In an alternative of the immediately preceding embodiment, m is 0. In another alternative of the immediately preceding embodiment, m is 1. In another alternative of the immediately preceding embodiment, m is 2.

In another alternative of the immediately preceding embodiment, n is 0. In another alternative of the immediately preceding embodiment, n is 1. In another alternative of the immediately preceding embodiment, n is 2.

In one embodiment, in each of Formulas (I), (I'), (IA), (IA'), (II), (II'), (IIA), (IIA'), (III), (III'), (IIIA), (IIIA'), (IV), (IV'), (IVA), and (IVA')

q=1;
-L$_1$- is —O—;
ring A is selected from the group consisting of phenyl and pyridinyl;
m is 0, 1, 2, or 3;
each $R^A$ (when present) is fluoro;
ring B is pyridinyl;
n is 0, 1, or 2; and
$R^B$ (when present) is fluoro.

In an alternative of the immediately preceding embodiment, m is 0. In another alternative of the immediately preceding embodiment, m is 1. In another alternative of the immediately preceding embodiment, m is 2.

In another alternative of the immediately preceding embodiment, n is 0. In another alternative of the immediately preceding embodiment, n is 1. In another alternative of the immediately preceding embodiment, n is 2.

In some embodiments, in each of Formulas (I), (I'), (IA), and (IA'):
q is 0. In these embodiments, the moiety:

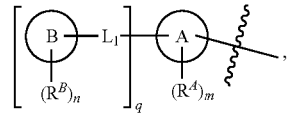

has the form:

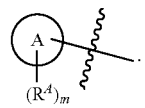

In one embodiment, in each of Formulas (I), (I'), (IA), and (IA'):
q=0;
ring A is selected from the group consisting of phenyl, pyridazinyl, pyridinyl, pyrimidinyl, pyrazinyl, pyrazolyl, triazinyl, thiazolyl, and thienyl;
m is 0, 1, 2, 3, or 4, provided that the value of m does not exceed the number of available substitutable hydrogen atoms on ring A; and
each $R^A$ (when present) is independently selected from the group consisting of fluoro, chloro, bromo, oxo, —OH, —CN, methyl, ethyl, propyl, butyl, —CH$_2$OCH$_3$, —CH$_2$OCF$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$NHCH$_2$CF$_3$, —CF$_3$, —CHF$_2$, —CH$_2$F, —NH$_2$, —NH$_2$CH$_2$CF$_3$, —NHC(O)CH$_3$, —NHC(O)CHF$_2$, —NHC(O)CH$_2$OCH$_3$, —OCH$_3$, —OCH$_2$CH$_3$, —OCH$_2$CH$_2$CH$_3$, —OCH$_2$CH(CH$_3$)$_2$, —OCH$_2$CH$_2$OCH$_3$, —OCF$_3$, —OCHF$_2$, —OCH$_2$F, —OCH$_2$CF$_3$, —OCH$_2$CHF$_2$, —OCH$_2$CH$_2$F, and —OCH$_2$CH$_2$CF$_3$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3, provided that the value of m does not exceed the number of available substitutable hydrogen atoms on ring A. In another alternative of the immediately preceding embodiment, m is 4, provided that the value of m does not exceed the number of available substitutable hydrogen atoms on ring A.

In one embodiment, in each of Formulas (I), (I'), (IA), and (IA'):

q=0;

ring A is selected from the group consisting of phenyl and pyridinyl;

m is 0, 1, 2, or 3; and each $R^A$ (when present) is independently selected from the group consisting of fluoro, bromo, —OH, —CN, —NH$_2$, —NHC(O)CHF$_2$, —NHC(O)CH$_2$OCH$_3$, —CH$_2$NHCH$_2$CF$_3$, —OCH$_2$OCH$_3$, —OCH$_2$CF$_3$, and —OCH$_2$CH$_2$CF$_3$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):

q=0;

ring A is selected from the group consisting of phenyl and pyridinyl;

m is 0, 1, 2, or 3; and each $R^A$ (when present) is independently selected from the group consisting of fluoro, bromo, —NHC(O)CHF$_2$, —NHC(O)CH$_2$OCH$_3$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

Specific non-limiting examples of compounds of the invention are shown in the table of examples below. While only one tautomeric form of each compound is shown in the tables, it shall be understood that both tautomeric forms of the compounds corresponding to those of Formulas (I) and (I') are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from β$_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., m$_1$ agonists (such as acetylcholine, oxotremorine, carbachol, or McNa343), or m$_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; GABA$_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting β-secretase comprising exposing a population of cells expressing β-secretase to at least one compound of the invention, or a tautomer thereof, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease.

In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a compound of the invention, or a pharmaceutically acceptable salt thereof, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to about 10 carbon atoms. "Lower alkyl" means a straight or branched alkyl group comprising 1 to 6 carbon atoms. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, i-butyl, and t-butyl.

"Cycloalkyl" means a non-aromatic monocyclic or multicyclic ring system comprising 3 to about 10 carbon atoms, preferably 3 to 6 ring carbon atoms. Non-limiting examples of 3-, 4-, 5-, and 6-membered cycloalkyl groups include cyclopropyl, cyclobutyl, cyclopentyl, and cyclohexyl, respectively. Non-limiting examples of multicyclic cycloalkyls include [1.1.1]-bicyclopentane, 1-decalinyl, norbornyl, adamantyl and the like. "Lower cycloalkyl" means cyclopropyl, cyclobutyl, and cyclopentyl.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl moiety or the like includes substitution on any ring portion and/or on the alkyl portion of the group.

When a variable appears more than once in a group, e.g., $R^6$ in $-N(R^6)_2$, or a variable appears more than once in a structure presented herein, the variables can be the same or different.

The solid line —, as a bond generally indicates a mixture of, or either of, the possible isomers, e.g., containing (R)- and (S)-stereochemistry. For example:

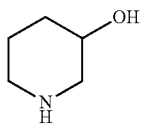

implies

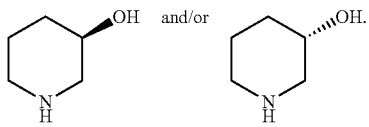

The wavy line ~~~, as used herein, indicates a point of attachment to the rest of the compound. Lines drawn into the ring systems, such as, for example:

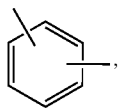

indicate that the indicated line (bond) may be attached to any of the substitutable ring carbon (or ring hetero) atoms.

"Oxo" is defined as a oxygen atom that is double bonded to a ring carbon in a cycloalkyl, cycloalkenyl, heterocyclyl, heterocyclenyl, or other ring described herein, e.g.,

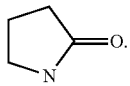

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

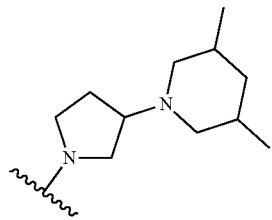 [SMILES: *N1CCC(N2CC(C)CC(C)C2)C1]

represents

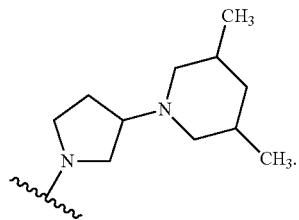 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, *"Pro-drugs as Novel Delivery Systems,"* Vol. 14 of the A.C.S. Symposium Series, and in *Bioreversible Carriers in Drug Design*, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention. Thus, a compounds of the invention conforming to the formula:

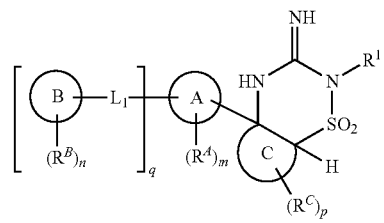

and its tautomer, which can be depicted as:

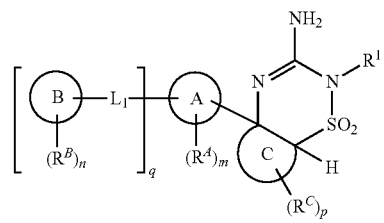

are both contemplated as being within the scope of the compounds of the invention. As noted above, while only one said tautomeric form of each compound is shown in the tables and appended claims, it shall be understood that both tautomeric forms of the compounds are contemplated as being within the scope of the non-limiting example compounds of the invention. Thus, as should be clear from the foregoing, the compounds of examples in the table below may alternatively be depicted, and exist, as their respective tautomers.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). For example, if a compound of the invention incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18<sup>th</sup> Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration. Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comprising one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted.

Abbreviations
Acetonitrile: MeCN
Aqueous: aq.
Benzyl: Bn
Bis(2-methoxyethyl)aminosulfur trifluoride: Deoxo-Fluor®
tert-Butyl: t-Bu or tBu
tert-Butyldimethylsilyl chloride: TBSCl
tert-Butoxycarbonyl: t-Boc or Boc
di-tert-butyldicarbonate: (Boc)$_2$O
Chloro(2-dicyclohexylphosphino-2',6'-diisopropoxy-1,1'-biphenyl)[2-(2'-amino-1,1'-biphenyl)]palladium(II): RuPhos G2 precatalyst
Dichloromethane: DCM
[2-(Di-1-adamantylphosphino)-2',4',6'-triisopropyl-3,6-dimethoxybiphenyl][2-(2'-amino-1,1'-biphenyl)]palladium(II) methanesulfonate: Ad-BrettPhos G3 precatalyst
[(2-Di-cyclohexylphosphino-3,6-dimethoxy-2',4',6'-triisopropyl-1,1'-biphenyl)-2-(2'-amino-1,1'-biphenyl)]palladium(II) methanesulfonate: BrettPhos G3 precatalyst
Diisopropylethylamine: DIEA, DIEPA or iPr$_2$Net
N,N-dimethylaminopyridine: DMAP
Dimethylformamide: DMF
Dimethylformamide-dimethyl acetal: DMF-DMA
Dimethylsulfoxide: DMSO
Ether or diethyl ether: Et$_2$O
Ethyl: Et
Ethyl acetate: AcOEt, EtOAc, or EA
1-Ethyl-3-(3-dimethylaminopropyl)carbodiimide: EDCI
1-Ethyl-2,2,4,4,4-pentakis(dimethylamino)-2$\lambda^5$,4$\lambda^5$-catenadi(phosphazene),
Tetramethyl(tris(dimethylamino)phosphoranylidene)phosphorictriamid-Et-imin: P2-Et
phosphazene base Example: Ex.
Grams: g
Hexanes: hex
High performance liquid chromatography: HPLC
Inhibition: Inh.
Killogram: kg
Lithium bis(trimethylsilyl)aride: LiHMDS
Methanesulfonyl chloride: MeSO$_2$Cl or MsCl
Methanol: MeOH
Methoxyethoxymethyl: MEM
Methoxyethoxymethyl chloride: MEMCl
Methyl chloromethyl ether: MOMCl
Methyl iodide: MeI
Microliters: µl or µL
Milligrams: mg
Milliliters: mL
Millimoles: mmol
Minutes: min
n-Butyllithium: nBuLi or n-BuLi
Nuclear magnetic resonance spectroscopy: NMR
Para-methoxy benzyl: PMB
Petroleum ether: PE
1-Propanephosphonic anhydride: T3P
Potassium tert-butoxide: KOtBu
Pyridinium chlorochromate: PCC
Saturated: sat.
Tetrabuylammonium fluoride: TBAF

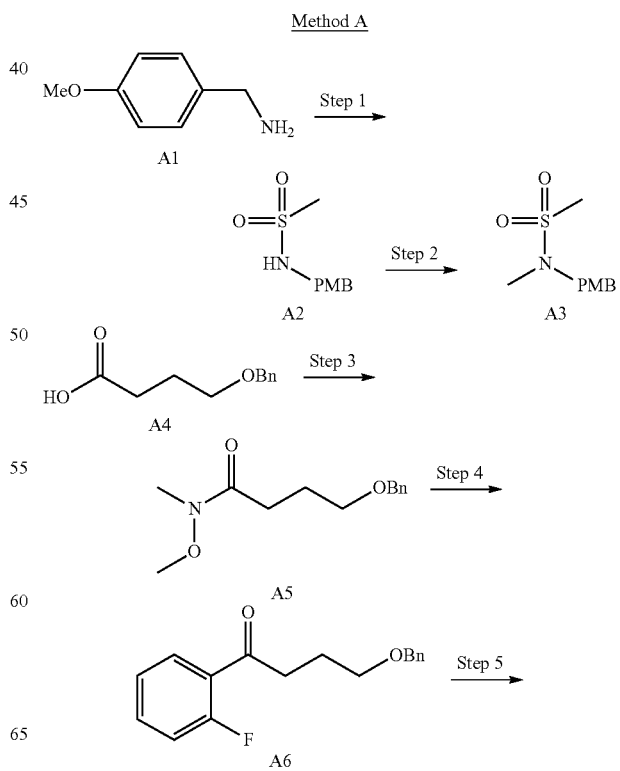

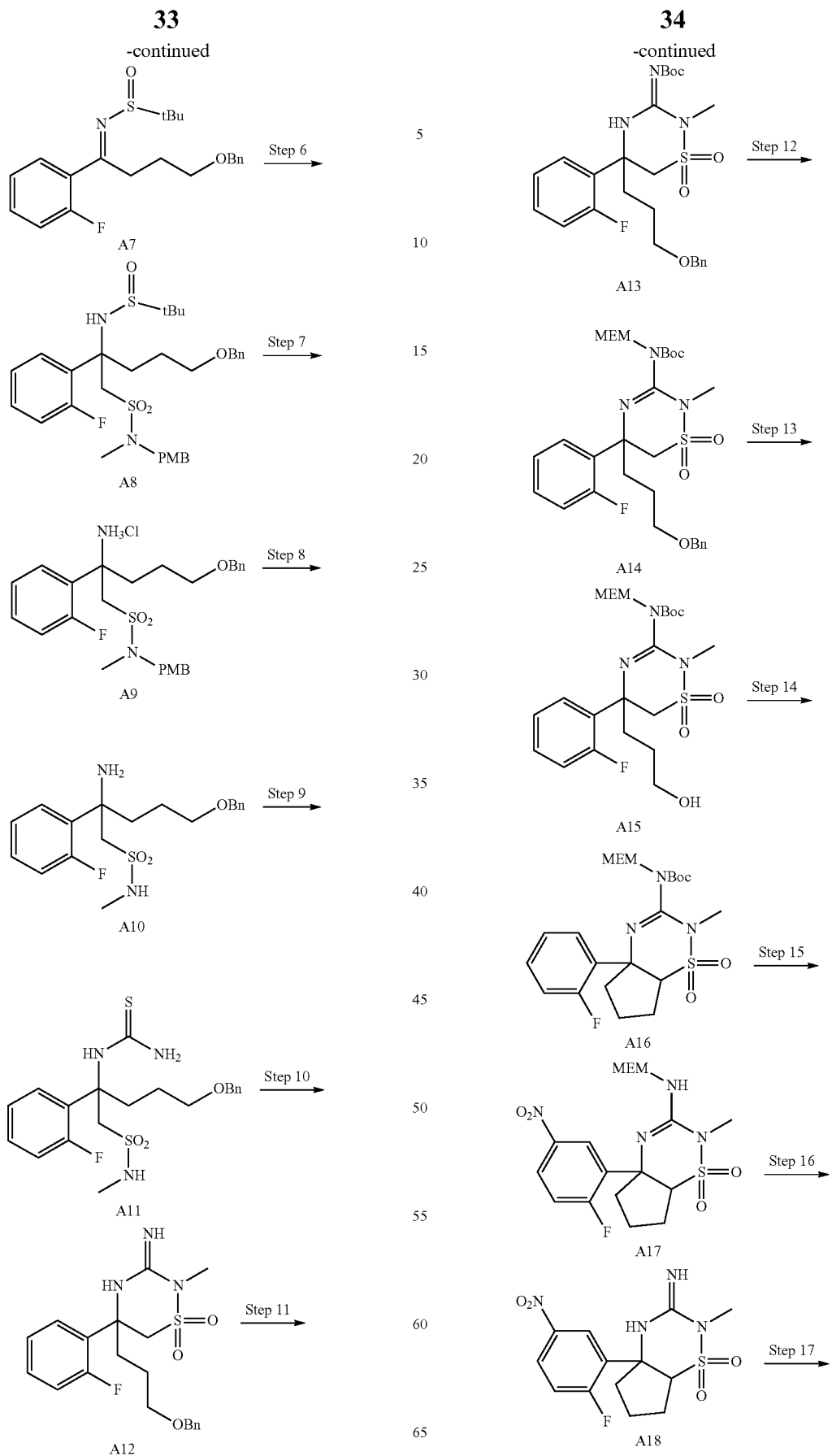

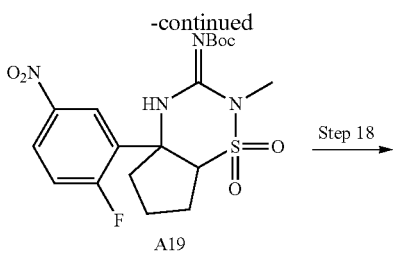

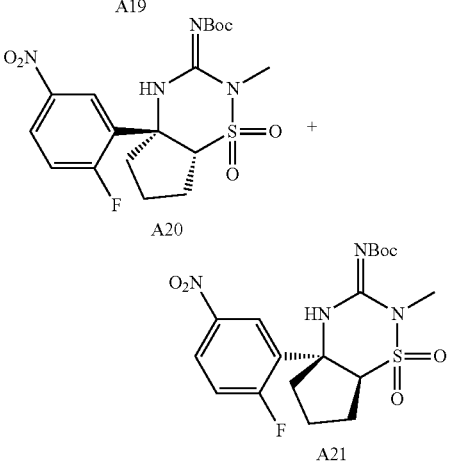

Step 1: Into a 5-L 4-necked round-bottom flask purged and maintained with an inert atmosphere of nitrogen, was placed A1 (500 g, 3.64 mol) and pyridine (1000 mL) at 0° C. This was followed by the addition of methanesulfonyl chloride (440 g, 3.84 mol) dropwise with stirring at 0° C. over 60 min. The resulting solution was stirred for 4 h at room temperature and then concentrated under reduced pressure. The residue was dissolved in 4000 mL of DCM. The resulting mixture was washed sequentially with 1N HCl (aq.) (2×2000 mL), NaHCO$_3$ (aq.) (2×2000 mL), and brine (1×1000 mL). The organic layer was then dried over anhydrous Na$_2$SO$_4$ and concentrated under reduced pressure. The product, A2, was carried on without further purification.

Step 2: Into a 10-L 4-necked round-bottom flask purged and maintained under an atmosphere of nitrogen, was placed a solution of A2 (640 g, 2.97 mol) in DMF (3200 mL). The reaction was cooled to 0° C. This was followed by the addition of Cs$_2$CO$_3$ (1450 g, 4.46 mol). To the mixture was then added iodomethane (1060 g, 7.44 mol) dropwise over 30 min with stirring at 0° C. The resultant mixture was stirred overnight at room temperature and then poured into 50 L of water/ice. The solid product was collected by filtration and washed with water (2×5 L). The residue was dissolved in 5000 mL of DCM. The resulting mixture was washed with brine (2×1000 mL), dried over Na$_2$SO$_4$ and concentrated under reduced pressure to afford A3. This material was carried on without further purification.

Step 3: Into a 20-L 4-necked round-bottom flask purged and maintained under an inert atmosphere of nitrogen, was placed a solution of A4 (750 g, 3.86 mol, 1.00 equiv) in dichloromethane (7 L). This was followed by the addition of N,N-carbonyldiimidazole (752 g, 4.64 mol) in portions at room temperature over 20 min. To this was added N,O-dimethylhydroxylamine hydrochloride (455 g, 4.69 mol) in portions at room temperature over 20 min. The resultant mixture was stirred for 24 h at room temperature and then poured into 7 L of water/ice. The mixture was extracted with DCM (2×4.0 L) and the combined organic layers were washed with water (2×4.0 L), dried over anhydrous Na$_2$SO$_4$ and concentrated under reduced pressure. The crude residue was purified by column chromatography (SiO$_2$; 1:5 EtOAc:petroleum ether) to afford A5.

Step 4: Into a 10-L 4-necked round-bottom flask purged and maintained under an atmosphere of nitrogen, was placed a solution of 1-bromo-2-fluorobenzene (738 g, 4.22 mol) in THF (3 L). The solution was cooled to −70° C. To the solution was then added a solution of n-BuLi (2.5 M, 1.68 L) dropwise with stirring at −70° C. over 40 min. The reaction mixture was stirred for 60 min at −70° C. To this was added a solution of A5 (400 g, 1.69 mol) in THF (2 L) dropwise over 40 min with stirring at −70° C. The resultant solution was stirred for 2 h at −70° C. The reaction was then quenched by the addition of 3 L of an aqueous NH$_4$Cl solution. The resultant solution was extracted with EtOAc (2×4 L) and the combined organic layers were washed with water (1×3 L), dried over anhydrous Na$_2$SO$_4$ and concentrated under reduced pressure. The crude residue was purified by column chromatography (SiO$_2$; 1:30 EtOAc:hexanes) to afford A6.

Step 5: Into a 20-L 4-necked round-bottom flask purged and maintained with an inert atmosphere of nitrogen, was placed a solution of A6 (600 g, 2.20 mol) in THF (6.0 L), followed by Ti(OEt)$_4$ (1500 g, 6.6 mol) and 2-methylpropane-2-sulfinamide (530 g, 4.4 mol). The resultant mixture was heated to reflux for 24 hr. The reaction mixture was then cooled to room temperature with a water bath. The resulting solution was diluted with 3.5 L of EtOAc and then poured into 10 L of water/ice. The solid was filtered out and then filtrate was extracted with EtOAc (2×3 L). The combined organic layers were washed with water (2×4 L), dried over anhydrous sodium sulfate and concentrated under vacuum. The residue was purified by column chromatography (SiO$_2$; 1:10 EtOAc:petroleum ether) to afford A7.

Step 6: Into a 10-L 4-necked round-bottom flask purged and maintained with under an atmosphere of nitrogen, was placed a solution of A3 (228 g, 0.99 mol) in THF (2.75 L). The solution was cooled to at −70° C. To the solution was then added a solution of n-BuLi (410 mL, 2.5 M) dropwise with stirring at −70° C. over 60 min. After the addition was complete, the reaction mixture was stirred at −70° C. for 0.5 h. After that time, a solution of A7 (275 g, 732.36 mmol, 1.00 equiv) in toluene (2.75 L) was added dropwise with stirring at −70° C. over 40 min. The resultant solution was stirred for 1.5 h at −70° C. and then warmed to −15° C. and stirred for an additional 1.5 hours. The reaction was then quenched by the addition of 2 L of aq. NH$_4$Cl. The mixture was extracted with ethyl acetate (3×1.5 L) and the combined organic layers were washed with H$_2$O (1×2 L), dried over anhydrous Na$_2$SO$_4$ and concentrated under reduced pressure. The crude residue was purified by column chromatography (SiO$_2$; 1:5 EtOAc:petroleum ether) to afford A8.

Step 7: Into a 10-L 4-necked round-bottom flask, was placed a solution of A8 (350 g, 579 mmol) in dichloromethane (3.0 L). The solution was cooled to 0° C. To the solution was added a solution of HCl in 1,4-dioxane (4M, 2 L) dropwise with stirring at 0° C. over 30 min. The resulting solution was stirred for 2 h at room temperature and then concentrated under reduced pressure to afford A9. This material was carried on without purification.

Step 8: Into a 5-L 4-necked round-bottom flask, was placed a solution of A9 (350 g, 554 mmol) in trifluoroacetic acid (3.5 L). This was followed by the addition of thioglycolic acid (601 g, 6.53 mol) dropwise with stirring at 0° C. in 20 min. The resultant solution was stirred overnight at room temperature and then concentrated under reduced pressure. The pH of the mixture was adjusted to 8 with a solution of 10% sodium bicarbonate. The resultant mixture was extracted with of dichloromethane (3×3 L). The combined organic layers were dried over anhydrous $Na_2SO_4$ and concentrated under reduced pressure. The crude residue was purified by column chromatography ($SiO_2$; 10:1 DCM:MeOH) to afford A10.

Step 9: Into a 5-L 4-necked round-bottom flask purged and maintained under an atmosphere of nitrogen, was placed a solution of A10 (200 g, 526 mmol) in dichloromethane (2.0 L). This was followed by the addition of benzoyl isothiocyanate (103 g, 631 mmol). The resultant solution was stirred at RT overnight and then concentrated under reduced pressure. To the residue was added methanol (2.0 L), dichloromethane (200 mL) followed by a solution of sodium methoxide (30 wt % in methanol, 280 mL). The resultant solution was stirred for 3 h at room temperature and then concentrated under reduced pressure. The pH of the mixture was adjusted to ~7 with 1.5 M HCl(aq.). The resultant mixture was extracted with dichloromethane (3×3 L) and the combined organic layers were dried over $Na_2SO_4$ and concentrated under reduced pressure to afford A11 that was taken on to the next step without further purification.

Step 10: Into a 5-L 4-necked round-bottom flask, was placed a solution of A11 (280 g, 318.50 mmol) in ethanol/DCM (2.8 L/280 mL) followed by methyl iodide (155 g, 1.10 mol). The resulting solution was stirred overnight at room temperature. The resultant solution was then heated to 60° C. with stirring for an additional 2 hours. After that time, the mixture was concentrated under reduced pressure. To the residue was added water (2 L). The pH of the mixture was adjusted to 8 with a solution of 10% sodium bicarbonate. The mixture was then extracted with dichloromethane (3×2 L). The combined organic layers were dried over anhydrous $Na_2SO_4$ and concentrated under reduced pressure. The crude residue was purified by column chromatography ($SiO_2$; 20:1 DCM:MeOH) to afford A12.

Step 11: Into a 5-L 3-necked round-bottom flask purged and maintained under an atmosphere of nitrogen, was placed a solution of A12 (105 g, 259 mmol) in dichloromethane (1.05 L). The solution was then cooled to 0° C. This was followed by the addition of N,N-diisopropylethylamine (167 g, 1.30 mol). To the solution was added a solution of $(Boc)_2O$ (168 g, 770 mmol) in dichloromethane (1.05 L) dropwise with stirring at 0° C. over 20 min. The resultant solution was stirred overnight at room temperature. After that time, the mixture was concentrated under reduced pressure. The crude residue was purified by column chromatography ($SiO_2$; 1:5 EtOAc:petroleum ether) to afford A13.

Step 12: Into a 2-L 4-necked round-bottom flask purged and maintained under an atmosphere of nitrogen, was placed a solution of A13 (75 g, 148 mmol) in THF (750 mL). This was followed by the addition of sodium hydride (8.5 g, 213 mmol 60% wt/wt) in portions at 25° C. over 30 min. The reaction mixture was stirred at 25° C. for 1 h. After that time, to the reaction mixture was added MEMCl (37.1 g, 297 mmol) dropwise with stirring at 25° C. over 30 min. The resultant solution was stirred for 2 h at room temperature. The reaction was then quenched by the addition of 300 mL of 10% aqueous $NaHCO_3$. The mixture was extracted with ethyl acetate (3×400 mL). The combined organic layers were dried over $Na_2SO_4$ and concentrated under reduced pressure to afford A14 which was carried on without further purification.

Step 13: Into a 2-L 4-necked round-bottom flask, was placed a solution of A14 (95 g, 128 mmolin methanol/DCM (1000 mL/200 mL) followed by $Pd(OH)_2$ (50 g), To the reaction mixture was stirred under a $H_2$ atmosphere overnight at RT. After that time, the mixture was filtered and the filtrate was concentrated under reduced pressure. The crude residue was purified by column chromatography ($SiO_2$; 2:1 EtOAc:petroleum ether) to afford A15.

Step 14: Into a 2-L 4-necked round-bottom flask purged and maintained under an atmosphere of nitrogen, was placed a solution of A15 (45 g, 89 mmol) in THF (750 mL). The mixture was cooled to 0° C. To the mixture was added $Et_3N$ (44.9 g, 445 mmol). followed by the addition of MsCl (20.4 g, 178 mmol) dropwise over 30 min. The reaction mixture was stirred at 0° C. for 2 h. After that time, to the mixture was added KOtBu (49.8 g, 445 mmol) in portions over 30 min at 0° C. The resultant solution was stirred for an additional 3 h at 0° C. The reaction was then quenched by the addition of 1 L of water/ice. The mixture was extracted with of ethyl acetate (3×500 mL) and the combined organic layers were washed with of a 10% $NH_4Cl$ solution (1×1000 mL) then dried over anhydrous $Na_2SO_4$ and concentrated under reduced pressure. The crude residue was purified by column chromatography ($SiO_2$; 1:5 EtOAc:petroleum ether) to afford A16.

Step 15: Into a 1-L 4-necked round-bottom flask, was placed A16 (24.3 g, 45.0 mmol). The flask was placed into a cooling bath at −30° C. This was followed by the addition of $HNO_3$ (160 mL) dropwise over 1 hour with stirring at −30° C. The resultant mixture was stirred for 4 h at −30° C. The reaction was then quenched by the addition of 1 kg of water/ice. The pH of the solution was adjusted to 8 by the addition of $NaHCO_3$ (solid). The resultant solid was filtered out and the filtrate was extracted with ethyl acetate (3×500 mL). The combined organic layer was dried over anhydrous $Na_2SO_4$ and concentrated under reduced pressure to afford A17 that was carried on without further purification.

Step 16: Into a 500-mL 3-necked round-bottom flask, was placed a solution of A17 (18.7 g, 36.9 mmolin trifluoroacetic acid (200 mL). The resultant solution was stirred overnight at 60° C. The reaction mixture was then concentrated under reduced pressure. The residue was dissolved in 1 L of $H_2O$ and the pH value of the solution was adjusted to 8 with $NaHCO_3$ (solid). The resultant mixture was extracted with ethyl acetate (3×500 mL) The organic layers combined and dried over $Na_2SO_4$ and concentrated under reduced pressure. The crude residue was purified by column chromatography ($SiO_2$; EtOAc) to afford A18.

Step 17: Into a 500-mL 3-necked round-bottom flask, was placed a solution of A18 (9.1 g, 27 mmol) in dichloromethane (90 mL) followed by DIEA (20.6 g, 159 mmol). The reaction mixture was then cooled to 0° C. This was followed by the addition of a solution of $Boc_2O$ (17.4 g, 79.8 mmol) in dichloromethane (90 mL) dropwise over 30 min with stirring at 0° C. The resulting solution was stirred overnight at room temperature and then concentrated under reduced pressure. The crude residue was purified by column chromatography ($SiO_2$; 1:5 EtOAc:petroleum ether) to afford A19. LC-MS (ES, m/z): 465 $[M+Na]^+$.

$^1$H-NMR: (400 MHz, $CDCl_3$, ppm): δ 10.641 (s, 1H), 8.411-8.436 (m, 1H), 8.267-8.307 (m, 1H), 7.283-7.333 (m, 1H), 4.38-4.426 (m, 1H), 3.327 (s, 3H), 2.533-2.633 (m, 2H), 2.283-2.371 (m, 2H), 2.105-2.163 (m, 2H), 1.584 (s, 9H).

Step 18: A19 was subjected to preparative chiral SFC separation (instrument: Thar 200 preparative SFC; Column: ChiralPak IC-10 um, 300×50 mm I.D.; mobile phase: 25% EtOH in CO₂; flow rate: 200 mL/min; back pressure: 100 bar; column temperature: 38° C. UV wavelength: 220 nm) to afford the individual enantiomers A20 and A21.

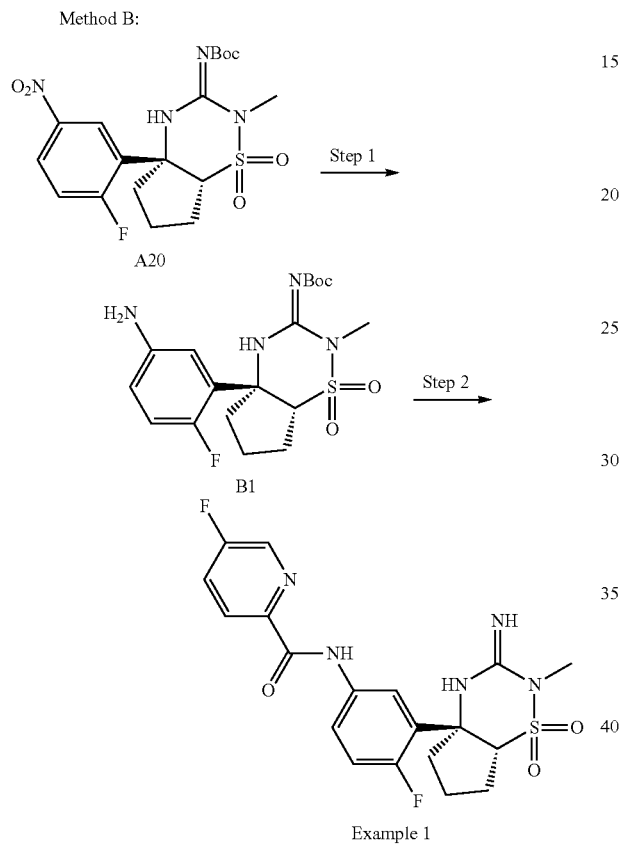

Example 1

Step 1: To a pressure release vial was added A20 (2.0 g, 4.52 mmol) followed by zinc powder (2.96 g, 45.2 mmol) and NH₄Cl (s) (1.21 g, 22.6 mmol). To the vial was then added a mixture of EtOH (10 ml), water (5 ml) and THF (20 ml). The vial was capped and placed into a preheated aluminum block at 70° C. The mixture was stirred at that temperature for 4 hours. The mixture was then allowed to cool to RT and filtered through a pad of celite. The filter cake was washed with EtOAc. The combined filtrates were then concentrated in vacuo. The resultant residue was partitioned between water and EtOAc and the aqueous layer was extracted with EtOAc (3×). The combined organic layers were washed with brine, dried over Na₂SO₄, filtered and concentrated. The crude product was purified by flash chromatography (SiO₂; gradient elution 100:0 to 1:1 hexanes:EtOAc) to afford B1.

Step 2: To a vial containing a solution of B1 (65 mg, 0.16 mmol) in DCM (2 ml) was added 5-fluoropicolinic acid (33 mg, 0.24 mmol) followed by DIPEA (83 µl, 0.47 mmol) and a solution of T₃P (50% in EtOAc, 190 µl, 0.32 mmol). The vial was capped and the mixture was stirred at RT overnight. After that time, to the vial was added water (100 µl, 5.6 mmol) followed by TFA (500 µl, 6.5 mmol). The mixture was stirred at RT for 2 hours. The mixture was then concentrated in vacuo. The residue was dissolved in 1 mL of DMSO, filtered and subjected to purification by mass triggered preparative HPLC. [column: Waters XBridge C18, 5 µm, 19×100 mm; solvent: gradient 25-60% MeCN (0.1% NH₄OH) in water (0.1% NH₄OH) 25 mL/min; 8 min run time] to afford Example 1.

| Ex | Structure IUPAC Name | LCMS m/z | BACE1 K$_i$ (nM) | BACE2 K$_i$ (nM) |
|---|---|---|---|---|
| 1 | | 436.13 | 10 | 1 |

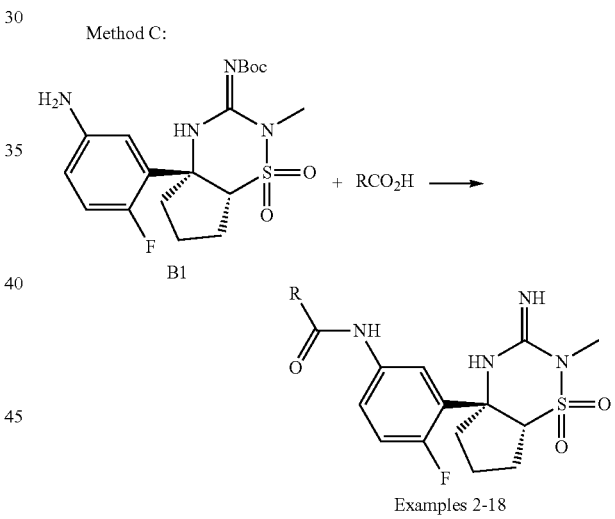

Examples 2-18

To a set of vials each containing the requisite carboxylic acid (0.11 mmol) was added a solution of B1 (30 mg, 0.073 mmol) in CH₂Cl₂ (1 mL). To each vial was then added diisopropylethylamine (38 µl, 0.22 mmol) followed by a solution of T₃P (50% in EtOAc, 87 µl, 0.15 mmol). The vials were capped and the mixtures were shaken at RT overnight. After that time to each vial was added water (50 µl, 2.78 mmol) followed by TFA (500 µl, 6.49 mmol). The mixtures were shaken at RT for 2.5 hours. The reaction mixtures were then concentrated under reduced pressure. Each residue was then dissolved in 1 mL of DMSO and filtered. The crude products were purified by mass triggered preparative HPLC [Waters Sunfire C18 column, 5 µm, 19×100 mm, using a gradient range from 10-20% initial to 45-55% final MeCN (0.1% TFA) in water (0.1% TFA), 25 mL/min 8 min run time] to afford Examples 2-18.

| Ex | Structure / IUPAC Name | LCMS m/z | BACE1 $K_i$ (nM) | BACE2 $K_i$ (nM) |
|---|---|---|---|---|
| 2 | N-(4-fluoro-3-((4aR,7aR)-3-imino-2-methyl-1,1-dioxidohexahydrocyclopenta[e][1,2,4]thiadiazin-4a(2H)-yl)phenyl)-5-(2-fluoroethoxy)pyrazine-2-carboxamide | 481.14 | 18 | 28 |
| 3 | 5-(difluoromethoxy)-N-(4-fluoro-3-((4aR,7aR)-3-imino-2-methyl-1,1-dioxidohexahydrocyclopenta[e][1,2,4]thiadiazin-4a(2H)-yl)phenyl)picolinamide | 484.12 | 4 | 6 |
| 4 | 5-chloro-N-(4-fluoro-3-((4aR,7aR)-3-imino-2-methyl-1,1-dioxidohexahydrocyclopenta[e][1,2,4]thiadiazin-4a(2H)-yl)phenyl)picolinamide | 452.09 | 3 | 1 |
| 5 | 5-cyano-N-(4-fluoro-3-((4aR,7aR)-3-imino-2-methyl-1,1-dioxidohexahydrocyclopenta[e][1,2,4]thiadiazin-4a(2H)-yl)phenyl)picolinamide | 443.12 | 4 | 3 |

-continued

| Ex | Structure IUPAC Name | LCMS m/z | BACE1 $K_i$ (nM) | BACE2 $K_i$ (nM) |
|---|---|---|---|---|
| 6 | N-(4-fluoro-3-((4aR,7aR)-3-imino-2-methyl-1,1-dioxidohexahydrocyclopenta[e][1,2,4]thiadiazin-4a(2H)-yl)phenyl)-5-methylpyrazine-2-carboxamide | 433.14 | 126 | 16 |
| 7 | N-(4-fluoro-3-((4aR,7aR)-3-imino-2-methyl-1,1-dioxidohexahydrocyclopenta[e][1,2,4]thiadiazin-4a(2H)-yl)phenyl)-5-methylpicolinamide | 432.14 | 42 | 3 |
| 8 | 5-chloro-3-fluoro-N-(4-fluoro-3-((4aR,7aR)-3-imino-2-methyl-1,1-dioxidohexahydrocyclopenta[e][1,2,4]thiadiazin-4a(2H)-yl)phenyl)picolinamide | 470.08 | 4 | 1 |
| 9 | 3,5-difluoro-N-(4-fluoro-3-((4aR,7aR)-3-imino-2-methyl-1,1-dioxidohexahydrocyclopenta[e][1,2,4]thiadiazin-4a(2H)-yl)phenyl)picolinamide | 454.11 | 22 | 1 |

| Ex | Structure IUPAC Name | LCMS m/z | BACE1 $K_i$ (nM) | BACE2 $K_i$ (nM) |
|---|---|---|---|---|
| 10 | 5-fluoro-N-(4-fluoro-3-((4aR,7aR)-3-imino-2-methyl-1,1-dioxidohexahydrocyclopenta[e][1,2,4]thiadiazin-4a(2H)-yl)phenyl)-3-methylpicolinamide | 450.13 | 10 | 1 |
| 11 | N-(4-fluoro-3-((4aR,7aR)-3-imino-2-methyl-1,1-dioxidohexahydrocyclopenta[e][1,2,4]thiadiazin-4a(2H)-yl)phenyl)-5-methoxy-3-methylpicolinamide | 462.15 | 16 | 1 |
| 12 | N-(4-fluoro-3-((4aR,7aR)-3-imino-2-methyl-1,1-dioxidohexahydrocyclopenta[e][1,2,4]thiadiazin-4a(2H)-yl)phenyl)-5-methoxy-3-methylpyrazine-2-carboxamide | 463.15 | 23 | 6 |
| 13 | 5-cyano-N-(4-fluoro-3-((4aR,7aR)-3-imino-2-methyl-1,1-dioxidohexahydrocyclopenta[e][1,2,4]thiadiazin-4a(2H)-yl)phenyl)-3-methylpicolinamide | 457.14 | 1 | 1 |

| Ex | Structure IUPAC Name | LCMS m/z | BACE1 $K_i$ (nM) | BACE2 $K_i$ (nM) |
|---|---|---|---|---|
| 14 | N-(4-fluoro-3-((4aR,7aR)-3-imino-2-methyl-1,1-dioxidohexahydrocyclopenta[e][1,2,4]thiadiazin-4a(2H)-yl)phenyl)-5-(trifluoromethyl)pyrazine-2-carboxamide | 487.11 | 25 | 40 |
| 15 | N-(4-fluoro-3-((4aR,7aR)-3-imino-2-methyl-1,1-dioxidohexahydrocyclopenta[e][1,2,4]thiadiazin-4a(2H)-yl)phenyl)-5-methoxypicolinamide | 448.14 | 16 | 3 |
| 16 | N-(4-fluoro-3-((4aR,7aR)-3-imino-2-methyl-1,1-dioxidohexahydrocyclopenta[e][1,2,4]thiadiazin-4a(2H)-yl)phenyl)-5-(2,2,2-trifluoroethoxy)pyrazine-2-carboxamide | 517.12 | 7 | 25 |
| 17 | N-(4-fluoro-3-((4aR,7aR)-3-imino-2-methyl-1,1-dioxidohexahydrocyclopenta[e][1,2,4]thiadiazin-4a(2H)-yl)phenyl)-5-methoxypyrazine-2-carboxamide | 449.13 | 11 | 8 |

| Ex | Structure IUPAC Name | LCMS m/z | BACE1 $K_i$ (nM) | BACE2 $K_i$ (nM) |
|---|---|---|---|---|
| 18 | N-(4-fluoro-3-((4aR,7aR)-3-imino-2-methyl-1,1-dioxidohexahydrocyclopenta[e][1,2,4]thiadiazin-4a(2H)-yl)phenyl)-5-(prop-2-yn-1-yloxy)picolinamide | 472.14 | 3 | 17 |

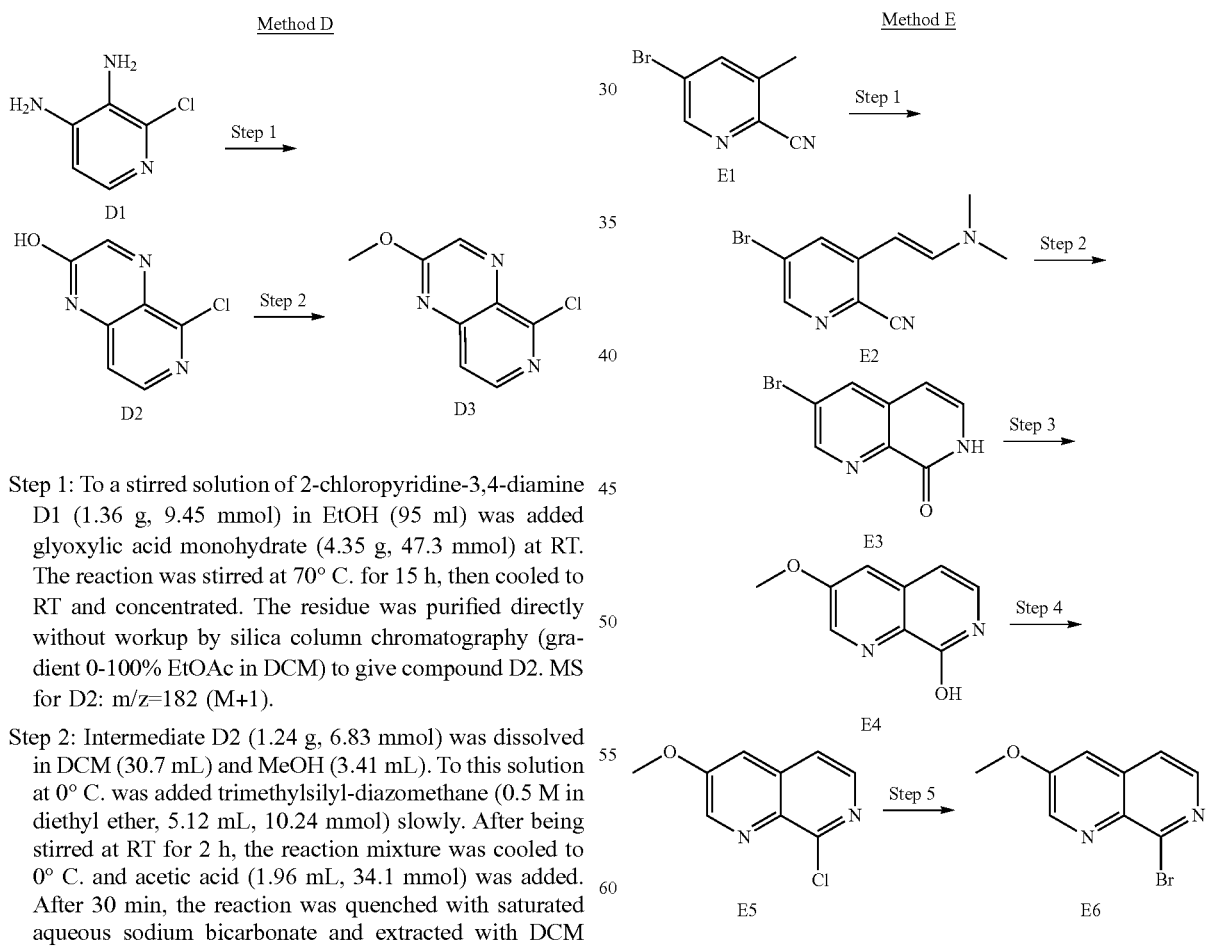

Step 1: To a stirred solution of 2-chloropyridine-3,4-diamine D1 (1.36 g, 9.45 mmol) in EtOH (95 ml) was added glyoxylic acid monohydrate (4.35 g, 47.3 mmol) at RT. The reaction was stirred at 70° C. for 15 h, then cooled to RT and concentrated. The residue was purified directly without workup by silica column chromatography (gradient 0-100% EtOAc in DCM) to give compound D2. MS for D2: m/z=182 (M+1).

Step 2: Intermediate D2 (1.24 g, 6.83 mmol) was dissolved in DCM (30.7 mL) and MeOH (3.41 mL). To this solution at 0° C. was added trimethylsilyl-diazomethane (0.5 M in diethyl ether, 5.12 mL, 10.24 mmol) slowly. After being stirred at RT for 2 h, the reaction mixture was cooled to 0° C. and acetic acid (1.96 mL, 34.1 mmol) was added. After 30 min, the reaction was quenched with saturated aqueous sodium bicarbonate and extracted with DCM three times. The combined organic layers were dried over magnesium sulfate, filtered, and concentrated. The crude residue was purified by silica column chromatography (0-30% EtOAc in hexanes) to afford compound D3. MS for D3: m/z=196 (M+1).

Step 1: To a solution of compound E1 (5.0 g, 25 mmol) in DMF (30 mL) was added DMF-DMA (6.8 mL, 50.8 mmol) at room temperature. The mixture was then stirred at 145° C. overnight and concentrated in vacuo to dryness.

The residue was purified by column chromatography (gradient PE:EA=50:1~10:1) to give compound E2.

Step 2: To a mixture of compound E2 (1.1 g, 4.4 mmol) in EtOH (9 mL) was added HBr (9 mL, 40% aq.) dropwise at room temperature. The mixture was stirred at reflux temperature for 4 h and cooled to room temperature. The precipitated solid was filtered and the filter cake was neutralized with sat. $Na_2CO_3$ until the evolved gas ceased. Then the mixture was filtered and the filter cake was dried to give compound E3. MS (M+H+): 225.

Step 3: A mixture of compound E3 (2.0 g, 8.89 mmol), sodium methanolate (2.40 g, 44.4 mmol) and copper(I) iodide (846 mg, 4.44 mmol) in DMF (20 mL) was stirred at 100° C. for 16 h under $N_2$. Then mixture was concentrated to give crude E4 which was used in the next step without further purification.

Step 4: Compound E4 (2.0 g, 8.0 mmol) was added to $POCl_3$ (30 mL, 322 mmol) and the mixture was stirred at 100° C. for 3 h. After that time, the mixture was concentrated and the residue was poured into water slowly, then neutralized with solid $Na_2CO_3$, and extracted with EtOAc. The combined organic extracts were washed with brine, dried over $Na_2SO_4$ and concentrated to give compound E5 which was used in the next step without further purification. MS (M+H$^+$): 195.

Step 5: To a suspension of compound E5 (900 mg, 4.62 mmol) in acetonitrile (10 mL) was added bromotrimethylsilane (7080 mg, 46.2 mmol). The mixture was stirred at 80° C. for 16 h. The resulting solid was filtered and washed with $Na_2CO_3$ (aq.) (10 mL) to give compound E6 that was used without further purification. MS (M+H$^+$): 239.

Method F

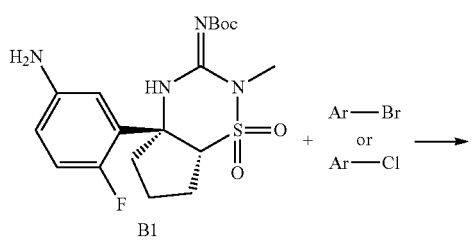

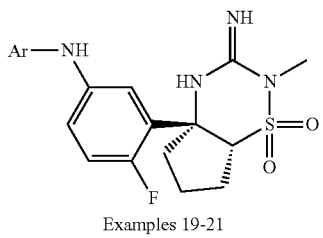

Examples 19-21

Parallel preparation of examples 19-21: To a set of vials containing the requisite aryl halide (0.15 mmol) was added Brettphos G3 precatalyst (6.6 mg, 0.0073 mmol) and RuPhos G2 precatalyst (5.6 mg, 0.0073 mmol). To each vial was then added a solution of B1 (30 mg, 0.073 mmol) in THF (1.0 mL). The vials were capped and transferred into a glove box under an atmosphere of nitrogen. To each vial was added sodium tert-butoxide (19 mg, 0.20 mmol). The mixtures were then heated at 50° C. with stirring overnight. After that time, water (2 mL) and DCM (2 mL) were added to each vial. The mixtures were transferred to a set of fritted barrel filters. The organic layer from each vial was drained into a clean vial. Additional DCM (1 mL) was added to each aqueous layer and the organic layer was again drained and combined with the previous organic extract. The solvent from the combined organic layers was removed in vacuo. To each vial was then added DCM (1 mL) and TFA (0.5 mL). The mixtures were stirred at RT for 2 hours. After that time, the mixtures were concentrated in vacuo. The crude residues were dissolved in DMSO (1 mL) and filtered. The crude products were purified by mass triggered preparative HPLC [Waters Sunfire C18 column, 5 μm, 19×100 mm, using a gradient range from 10% initial to 40-55% final MeCN (0.1% TFA) in water (0.1% TFA), 25 mL/min, 8-12 min run time] to afford Examples 19-21.

| Ex | ArBr or ArCl | Structure IUPAC Name | LCMS m/z | BACE1 $K_i$ (nM) | BACE2 $K_i$ (nM) |
|---|---|---|---|---|---|
| 19 | ![structure] | ![structure] (4aR,7aR)-4a-(2-fluoro-5-((3-methoxy-1,7-naphthyridin-8-ylamino)phenyl)-3-imino-2-methyloctahydrocyclopenta[e][1,2,4]thiadiazine 1,1-dioxide | 471.2 | 31 | 10 |

-continued

| Ex | ArBr or ArCl | Structure IUPAC Name | LCMS m/z | BACE1 $K_i$ (nM) | BACE2 $K_i$ (nM) |
|---|---|---|---|---|---|
| 20 | | (4aR,7aR)-4a-(2-fluoro-5-(2-methoxypyrido[3,4-b]pyrazin-5-ylamino)phenyl)-3-imino-2-methyloctahydrocyclopenta[e][1,2,4]thiadiazine 1,1-dioxide | 472.1 | 36 | 9 |
| 21 | | (4aR,7aR)-4a-(2-fluoro-5-((7-methoxy-1,5-naphthyridin-4-ylamino)phenyl)-3-imino-2-methyloctahydrocyclopenta[e][1,2,4]thiadiazine 1,1-dioxide | 471.2 | 206 | 198 |

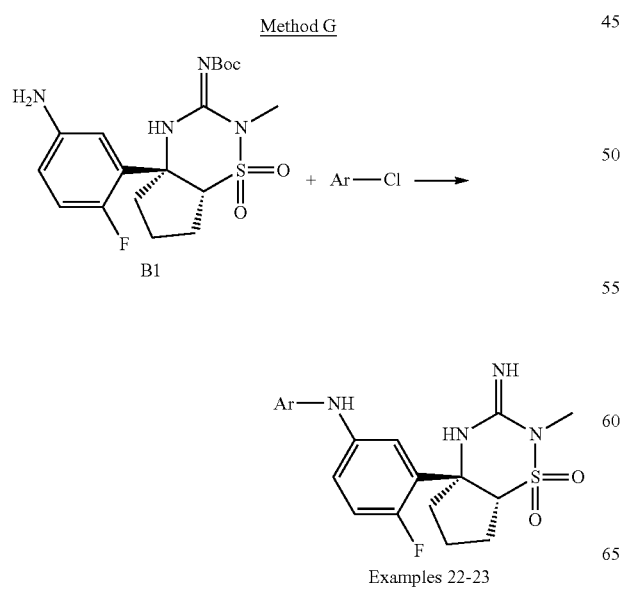

Method G

Examples 22-23

Parallel preparation of examples 22-23: To a set of vials containing the requisite aryl halide (0.15 mmol) was added a solution of B1 (30 mg, 0.073 mmol) in THF (1.0 mL). The vials were capped and transferred into a glove box under an atmosphere of nitrogen. To each vial was then added a solution of LHMDS (1.0 M in THF). The mixtures were then heated at 50° C. with stirring overnight. After that time, water (2 mL) and DCM (2 mL) were added to each vial. The mixtures were transferred to a set of fritted barrel filters. The organic layer from each vial was drained into a clean vial. Additional DCM (1 mL) was added to each aqueous layer and the organic layer was again drained and combined with the previous organic extract. The solvent from the combined organic layers was removed in vacuo. To each vial was then added DCM (1 mL) and TFA (0.5 mL). The mixtures were stirred at RT for 2 hours. After that time, the mixtures were concentrated in vacuo. The crude residues were dissolved in DMSO (1 mL) and filtered. The crude products were purified by mass triggered preparative HPLC [Waters Sunfire C18 column, 5 μm, 19×100 mm, using a gradient from 10% initial to 40% final MeCN (0.1% TFA) in water (0.1% TFA), 25 mL/min, 8 min run time] to afford Examples 22-23.

| Ex | ArCl | Structure IUPAC Name | LCMS m/z | BACE1 $K_i$ (nM) | BACE2 $K_i$ (nM) |
|---|---|---|---|---|---|
| 22 | 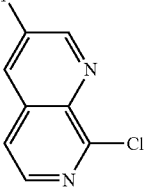 | 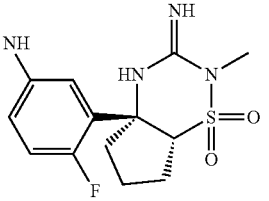 (4aR,7aR)-4a-(5-(((3-bromo-1,7-naphthyridin-8-yl)amino)-2-fluorophenyl)-3-imino-2-methyloctahydrocyclopenta[e][1,2,4]thiadiazine 1,1-dioxide | 518.1 | 4 | 0.5 |
| 23 | 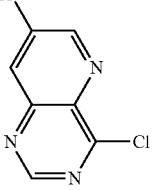 | 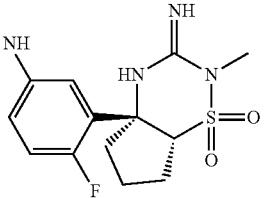 (4aR,7aR)-4a-(5-(((7-bromopyrido[3,2-d]pyrinaidin-4-ylamino)-2-fluorophenyl)-3-imino-2-methyloctahydrocyclopenta[e][1,2,4]thiadiazine 1,1-dioxide | 519.0 | 6 | 1 |
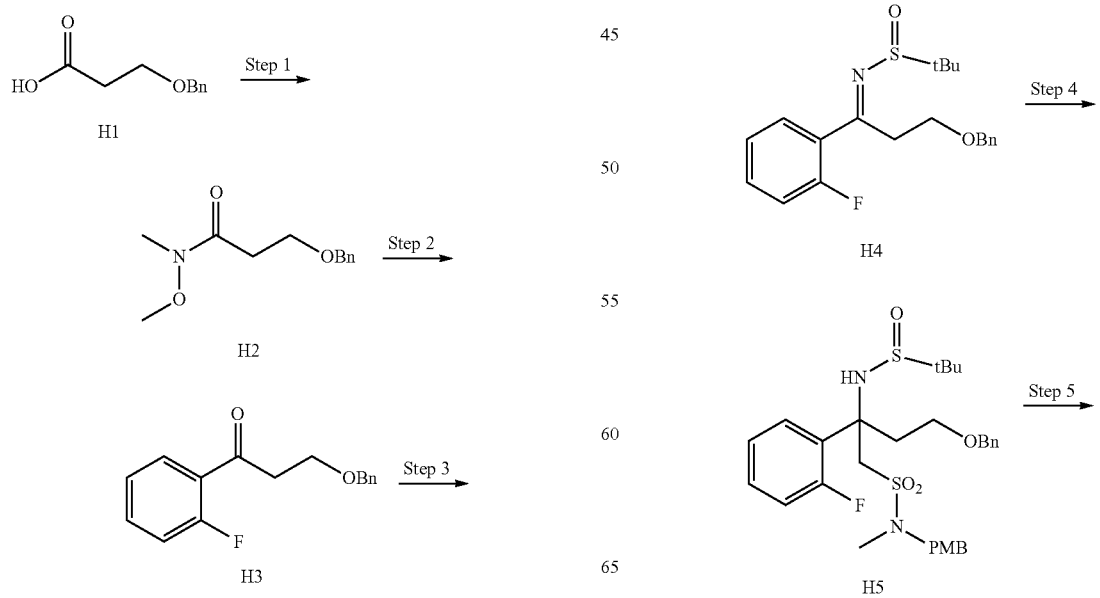
Method H

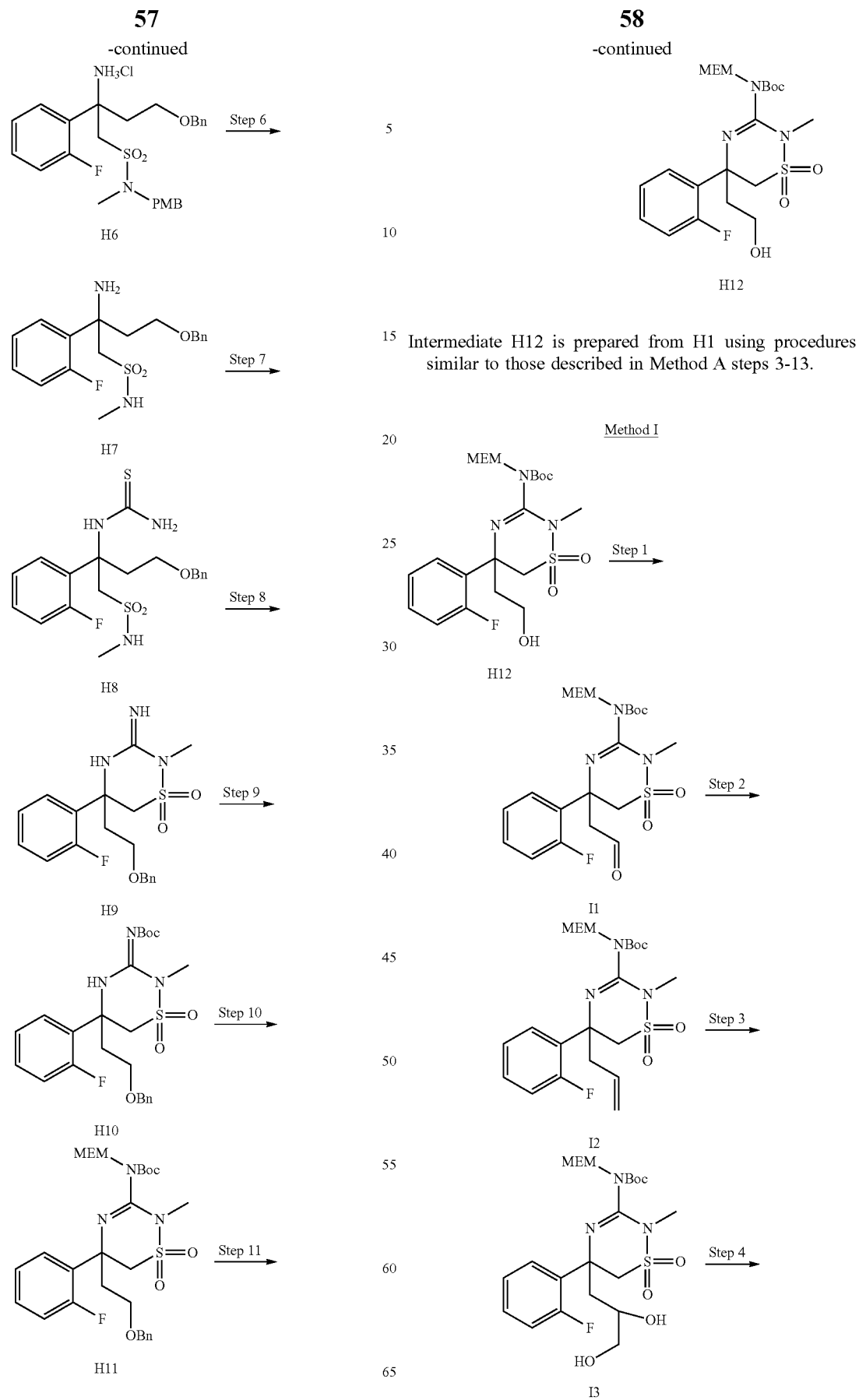
Intermediate H12 is prepared from H1 using procedures similar to those described in Method A steps 3-13.

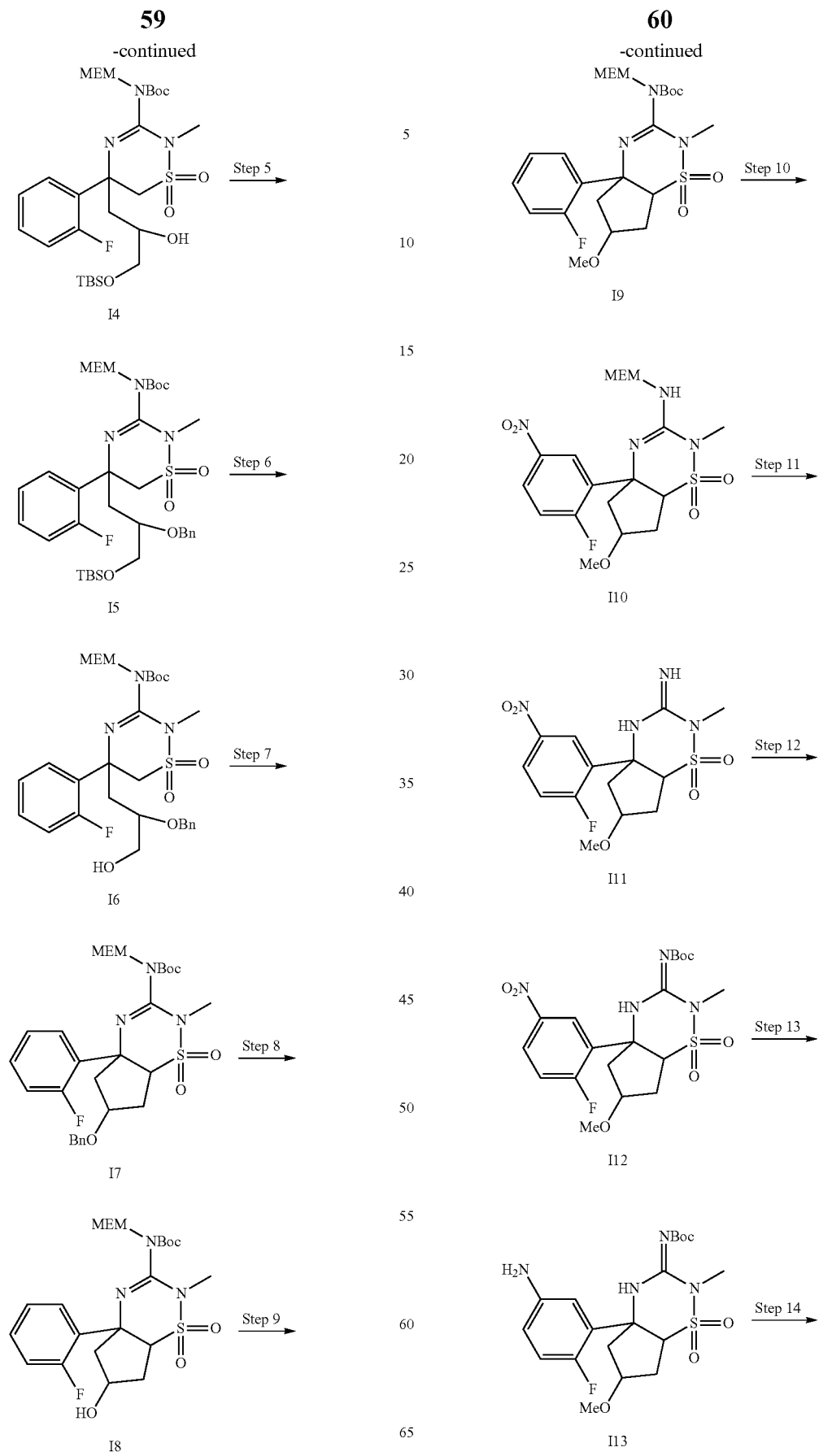

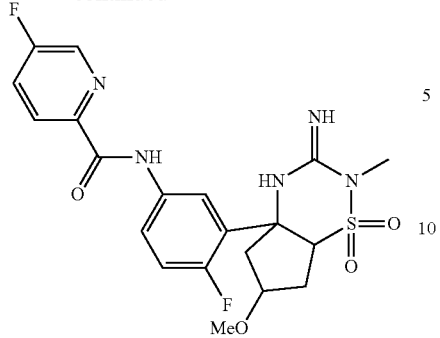

Example 24

Step 1: To a solution of H1 in DCM is added Dess-Martin periodinane. The resultant solution is stirred at RT for 3 hours. After that time, the mixture is washed with aq. $NaHCO_3$. The organic layer is dried over $Na_2SO_4$, filtered and concentrated. The crude residue is purified by flash silica gel chromatography to afford I1.

Step 2: To a solution of methyltriphenlyphosphonium bromide in THF at −20° C. is added a solution of n-BuLi (in hexanes). The resultant solution is stirred for 30 min. To the reaction mixture is then added a solution of I1 in THF. The resultant mixture is allowed to slowly warm to RT and stir overnight. The reaction mixture is washed with water and the aqueous layer is extracted with EtOAc (3×). The combined organic layers are dried over $Na_2SO_4$, filtered and concentrated. The crude residue is purified by flash silica gel chromatography to afford I2.

Step 3: To a mixture of I2 in t-BuOH/water is added potassium osmate(IV)dihydrate and 4-methyl-morpholine-N-oxide. The resultant mixture is stirred at RT overnight. After that time, the mixture is extracted with EtOAc (3×). The combined organic layers are dried over $Na_2SO_4$, filtered and concentrated. The crude residue is purified by flash silica gel chromatography to afford I3.

Step 4: To a solution of I3 in DMF is added TBSCl and imidazole. The reaction mixture is stirred at RT overnight. After that time, the reaction mixture is extracted with EtOAc (3×). The combined organic layers are dried over $Na_2SO_4$, filtered and concentrated. The crude residue is purified by flash silica gel chromatography to afford I4.

Step 5: To a solution of I4 in THF at RT is added NaH (60% in oil). The reaction mixture is stirred at RT for 30 min. After that time, benzyl bromide is added to the reaction mixture. The reaction is stirred at RT overnight. After that time, the reaction mixture is quenched slowly with water and the resultant mixture is extracted with EtOAc (3×). The combined organic layers are dried over $Na_2SO_4$, filtered and concentrated. The crude residue is purified by flash silica gel chromatography to afford I5.

Step 6: To a solution of I5 in THF at RT is added a solution of TBAF. The reaction mixture is stirred at RT for 3 hours. To the reaction mixture is added water. After that time, the reaction mixture is extracted with EtOAc (3×). The combined organic layers are dried over $Na_2SO_4$, filtered and concentrated. The crude residue is purified by flash silica gel chromatography to afford I6.

Step 7: To a solution of I6 in THF at 0° C. is added $Et_3N$. To this solution is added MsCl dropwise over 30 min with continued stirring at 0° C. The reaction mixture is stirred at 0° C. for 2 h. After that time, to the mixture is added KOtBu in portions over 30 min at 0° C. The resultant solution is stirred for an additional 3 h. After that time, the reaction mixture is quenched slowly with water and the mixture is extracted with EtOAc (3×). The combined organic layers are dried over $Na_2SO_4$, filtered and concentrated. The crude residue is purified by flash silica gel chromatography to afford I7.

Step 8: To a solution of I7 in MeOH is added $Pd(OH)_2$. The atmosphere is evacuated and backfilled with hydrogen. The reaction mixture is stirred at RT overnight under hydrogen. The reaction mixture is then purged with nitrogen, filtered, and concentrated in vacuo. The crude residue is purified by flash silica gel chromatography to afford I8.

Step 9: To a solution of I8 in THF is added NaH (60% in oil). The reaction mixture is stirred at RT for 30 min. After that time, methyl iodide is added to the reaction mixture. The reaction is stirred at RT overnight. After that time, the reaction mixture is quenched slowly with water and the resultant mixture is extracted with EtOAc (3×). The combined organic layers are dried over $Na_2SO_4$, filtered and concentrated. The crude residue is purified by flash silica gel chromatography to afford I9.

Steps 9-12: Intermediate I9 is converted to I12 following procedures similar to those described in Method A steps 15-17 respectively.

Steps 13-14: Intermediate I12 is converted to Example 24 following procedures similar to those described in Method B steps 1-2 respectively.

| Ex | Structure IUPAC Name | LCMS m/z | BACE1 $K_i$ (nM) | BACE2 $K_i$ (nM) |
|---|---|---|---|---|
| 24 | 5-fluoro-N-(4-fluoro-3-(3-imino-6-methoxy-2-methyl-1,1-dioxidohexahydrocyclopenta[e][1,2,4]thiadiazin-4a(2H)-yl)phenyl)picolinamide | — | — | — |

Method J

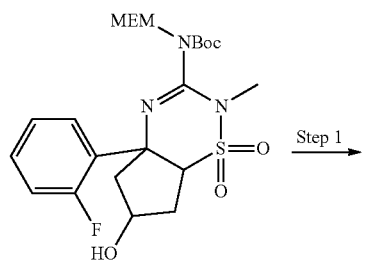

I8

-continued

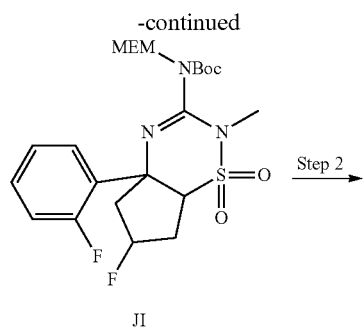

J1

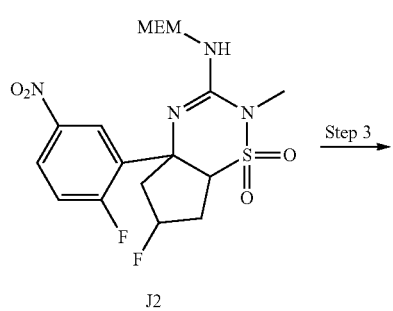

J2

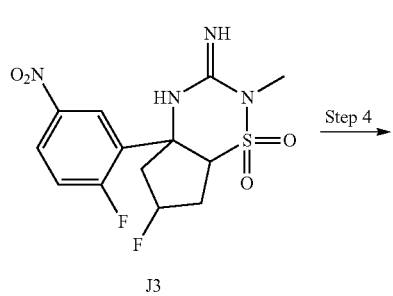

J3

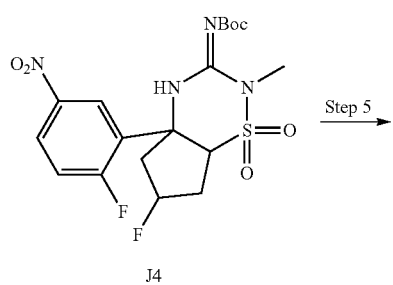

J4

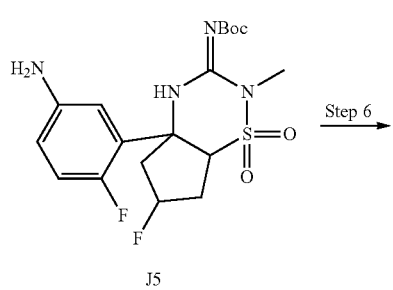

J5

-continued

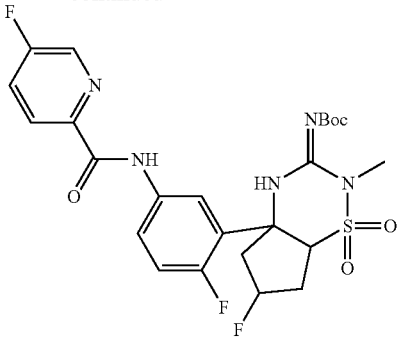

Example 25

Step 1: To a solution of I8 in DCM at −78° C. is added Deoxo-Fluor®. The reaction is stirred at −78° C. for 2 hours and allowed to slowly warm to RT. After 1 hour, the reaction mixture is quenched with aq. NaHCO$_3$. The mixture is extracted with DCM (3×). The combined organic layers are dried over Na$_2$SO$_4$, filtered and concentrated. The crude residue is purified by flash silica gel chromatography to afford J1.

Steps 2-4: Intermediate J1 is converted to J4 following procedures similar to those described in Method A steps 15-17 respectively.

Steps 13-14: Intermediate J4 is converted to Example 25 following procedures similar to those described in Method B steps 1-2 respectively.

| Ex | Structure IUPAC Name | LCMS m/z | BACE1 K$_i$ (nM) | BACE2 K$_i$ (nM) |
|---|---|---|---|---|
| 25 | 5-fluoro-N-(4-fluoro-3-(6-fluoro-3-imino-2-methyl-1,1-dioxidohexahydrocyclopenta[e][1,2,4]thiadiazin-4a(2H)-yl)phenyl)picolinamide | — | — | — |

Method K

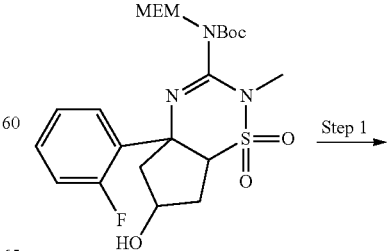

I8

-continued

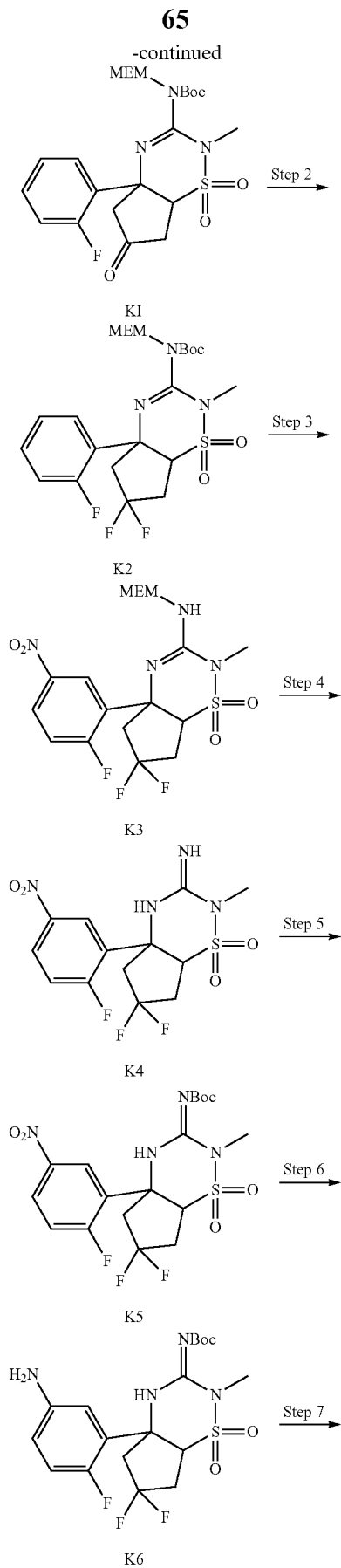

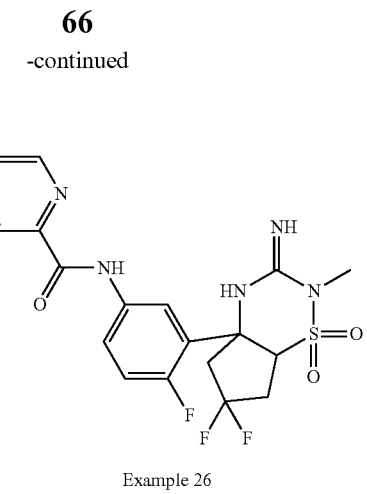

Example 26

Step 1. To a solution of I8 in DCM is added PCC. The mixture is stirred at RT for 3 hours then filtered through Celite. The mixture is then washed with aq. NaHCO$_3$. The mixture is extracted with DCM (3×). The combined organic layers are dried over Na$_2$SO$_4$, filtered and concentrated. The crude residue is purified by flash silica gel chromatography to afford K1.

Step 2. To a solution of K1 in DCE was added Deoxo-Fluor® followed by EtOH. The reaction is stirred at RT overnight. After that time, the reaction mixture is quenched with aq. NaHCO$_3$. The mixture is extracted with DCM (3×). The combined organic layers are dried over Na$_2$SO$_4$, filtered and concentrated. The crude residue is purified by flash silica gel chromatography to afford K2.

Steps 3-5: Intermediate K2 is converted to K5 following procedures similar to those described in Method A steps 15-17 respectively.

Steps 6-7: Intermediate K5 is converted to Example 26 following procedures similar to those described in Method B steps 1-2 respectively.

| Ex | Structure IUPAC Name | LCMS m/z | BACE1 K$_i$ (nM) | BACE2 K$_i$ (nM) |
|---|---|---|---|---|
| 26 | N-(3-(6,6-difluoro-3-imino-2-methyl-1,1-dioxidohexahydrocyclopenta[e][1,2,4]thiadiazin-4a(2H)-yl)-4-fluorophenyl)-5-fluoropicolinamide | — | — | — |

Method L

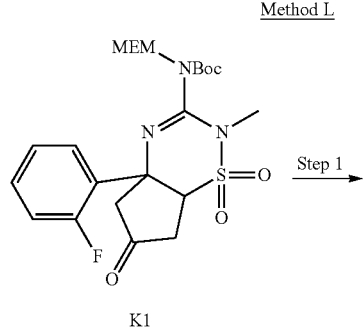

K1

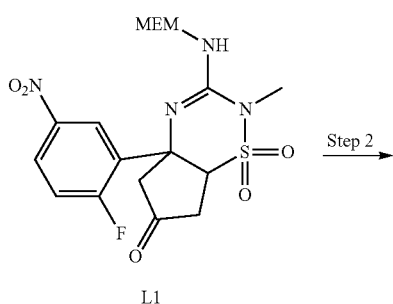

L1

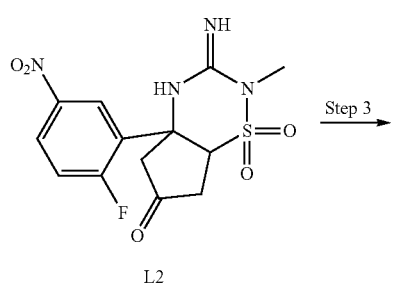

L2

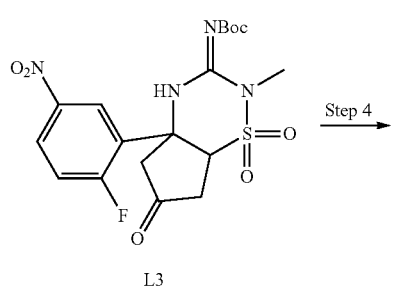

L3

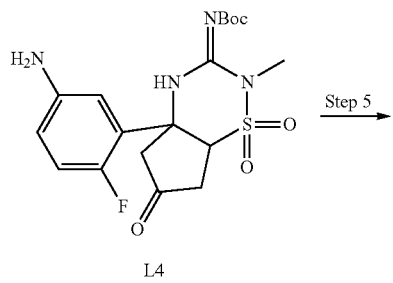

L4

-continued

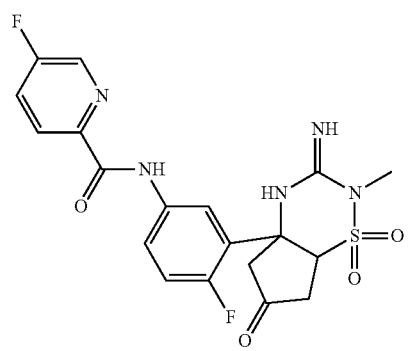

Example 27

Steps 1-3. Intermediate K1 is converted to L3 following procedures similar to those described in Method A steps 15-17 respectively.

Steps 4-5. Intermediate L3 is converted to Example 27 following procedures similar to those described in Method B steps 1-2 respectively.

| Ex | Structure IUPAC Name | LCMS m/z | BACE1 $K_i$ (nM) | BACE2 $K_i$ (nM) |
|---|---|---|---|---|
| 27 | 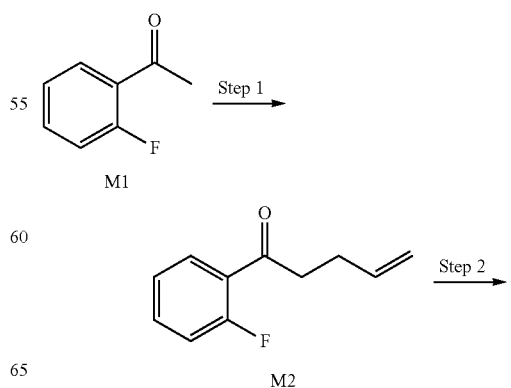

5-fluoro-N-(4-fluoro-3-(3-imino-2-methyl-1,1-dioxido-6-oxohexahydrocyclopenta[e][1,2,4]thiadiazin-4a(2H)-yl)phenyl)picolinamide | — | — | — |

Method M

-continued

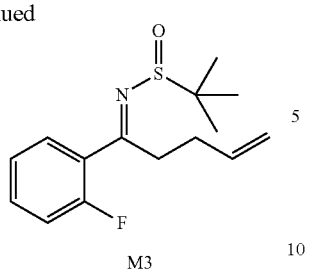

M3

Step 1: A literature procedure is adapted (*J. Am. Chem. Soc.*, 2005, 127, 8294).

A solution of 1-(2-fluorophenyl)ethanone M1 in THF is added to a suspension of potassium hydride in THF at 0° C. over 10 minutes. After 30 minutes, triethylboron is added and the mixture is stirred for an additional 15 minutes. Allyl bromide is then added and the reaction is allowed to warm to room temperature and is stirred for 4 h. The reaction mixture is quenched with a mixture (1:1) of 30% NaOH and 30% $H_2O_2$. The mixture is extracted with ether. The combined ether layers are washed with water and brine, dried (MgSO$_4$), filtered, and concentrated in vacuo. The residue is purified by silica gel chromatography to provide M2.

Step 2: To M2 in THF is added 2-methyl-2-propanesulfinamide and Ti(OEt)$_4$. The solution is heated to reflux and stirred for 12 h. The solution is cooled to room temperature and poured onto ice. To this mixture is added DCM and the resultant mixture is stirred for 10 minutes at room temperature. The mixture is extracted with DCM. The combined organic layers are washed with water and brine, dried (MgSO$_4$), filtered, and concentrated in vacuo. The residue is purified by silica gel chromatography to provide M3.

Scheme N

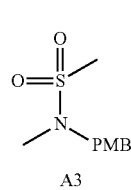 + 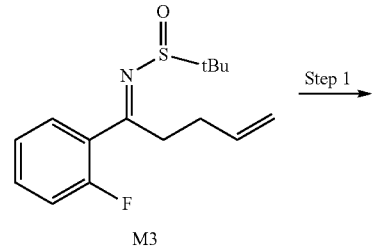 → Step 1

A3     M3

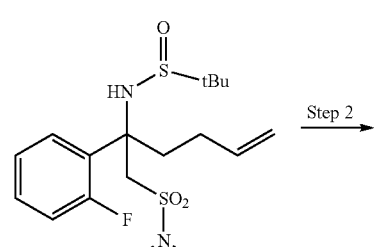

N1

-continued

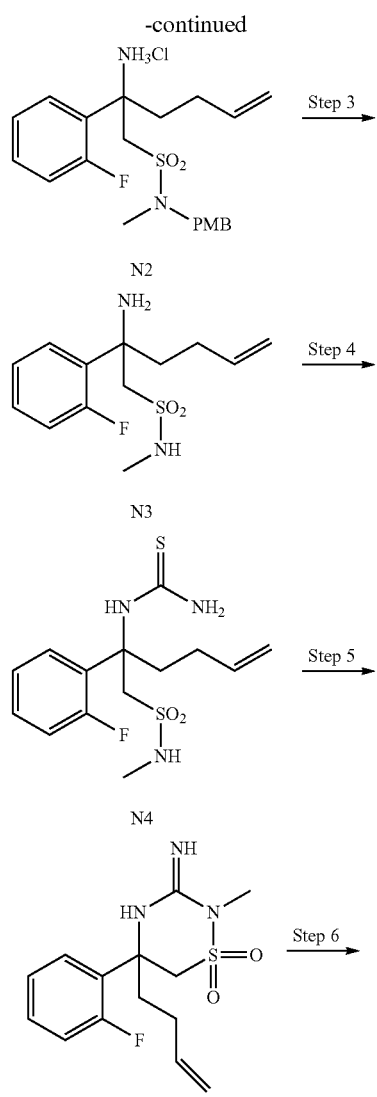

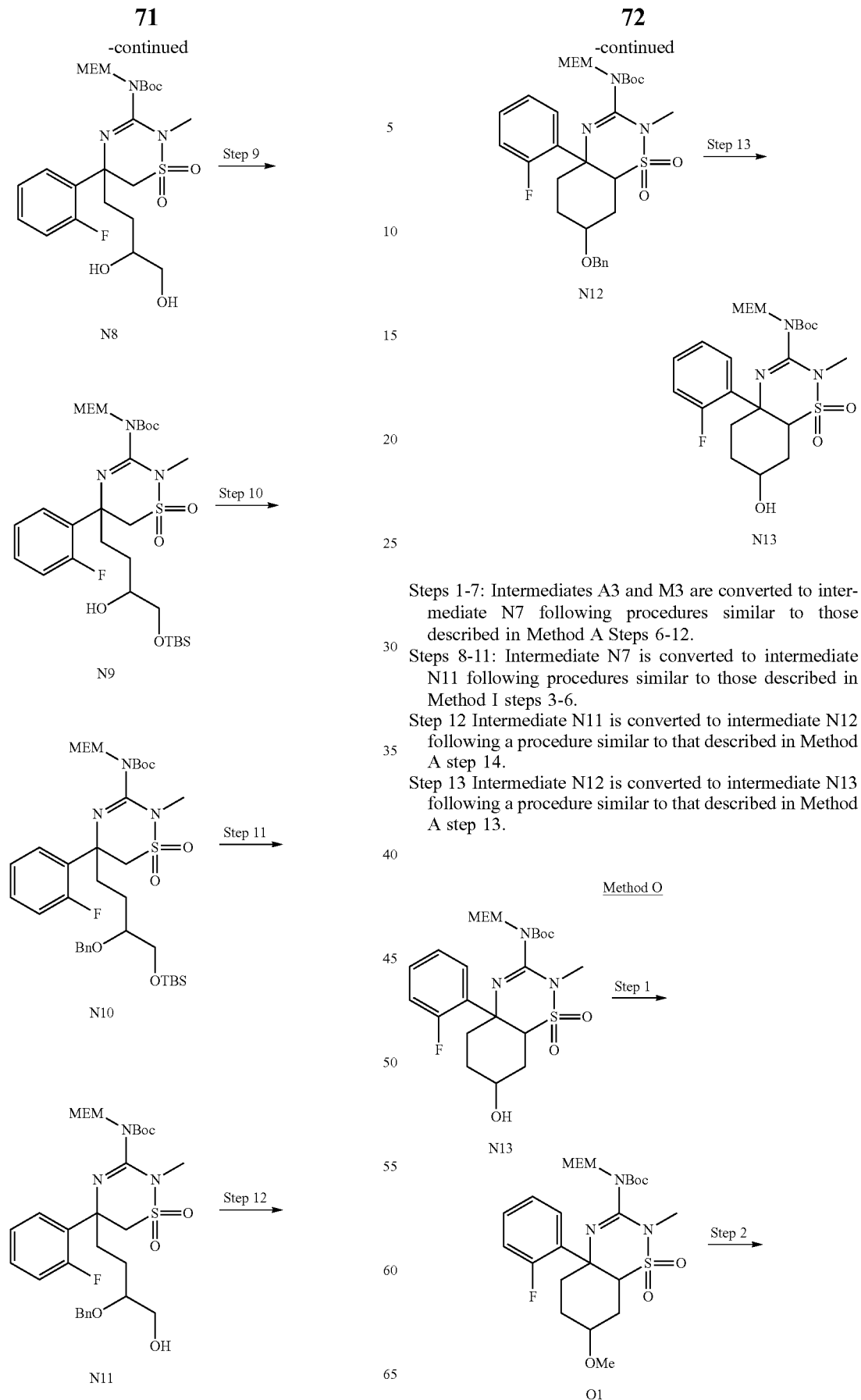

Steps 1-7: Intermediates A3 and M3 are converted to intermediate N7 following procedures similar to those described in Method A Steps 6-12.

Steps 8-11: Intermediate N7 is converted to intermediate N11 following procedures similar to those described in Method I steps 3-6.

Step 12 Intermediate N11 is converted to intermediate N12 following a procedure similar to that described in Method A step 14.

Step 13 Intermediate N12 is converted to intermediate N13 following a procedure similar to that described in Method A step 13.

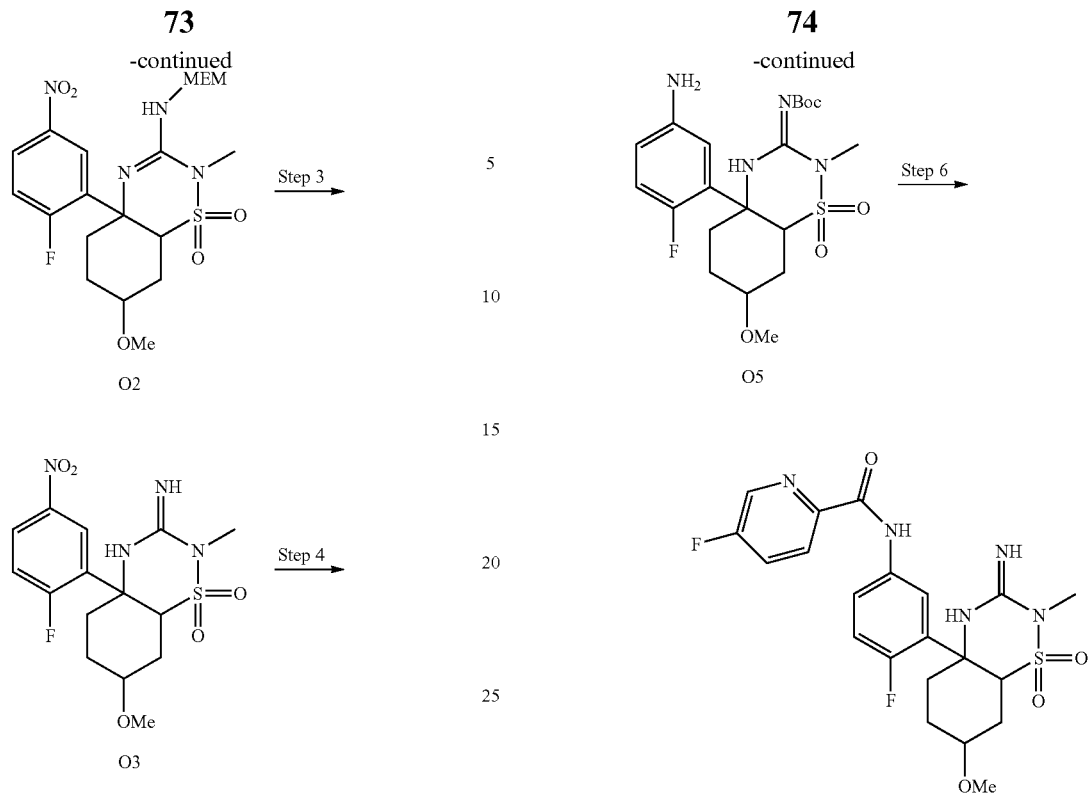

Step 1. Intermediate N13 is converted to intermediate O1 following a procedure similar to that described in Scheme I step 9.

Steps 2-4. Intermediate O1 is converted to O4 following procedures similar to those described in Method A steps 15-17 respectively.

Steps 5-6. Intermediate O4 is converted to Example 28 following procedures similar to those described in Method B steps 1-2 respectively.

| Ex | Structure IUPAC Name | LCMS m/z | BACE1 K<sub>i</sub> (nM) | BACE2 K<sub>i</sub> (nM) |
|---|---|---|---|---|
| 28 | 5-fluoro-N-(4-fluoro-3-(3-imino-7-methoxy-2-methyl-1,1-dioxidohexahydro-2H-benzo[e][1,2,4]thiadiazin-4a(5H)-yl)phenyl)picolinamide | — | — | — |

Method P

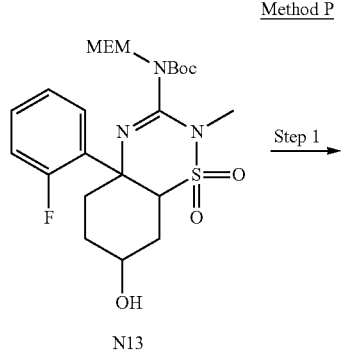
N13

Step 1 →

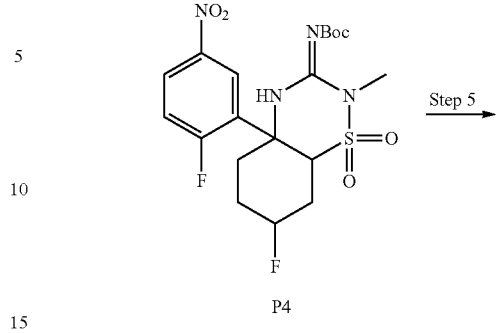
P4

Step 5 →

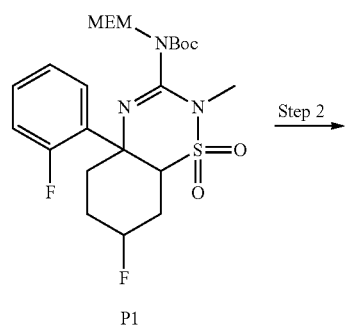
P1

Step 2 →

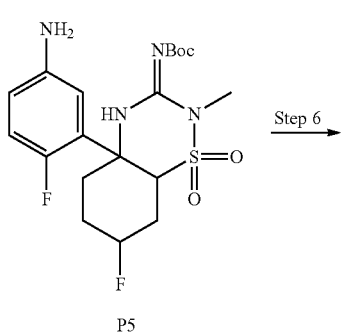
P5

Step 6 →

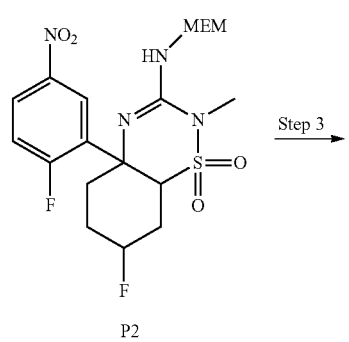
P2

Step 3 →

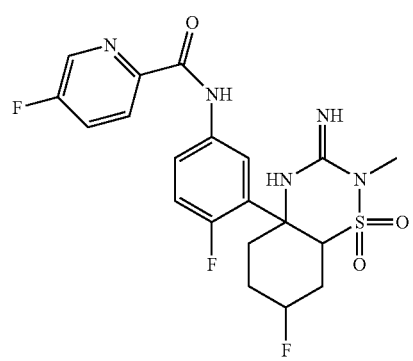
Example 29

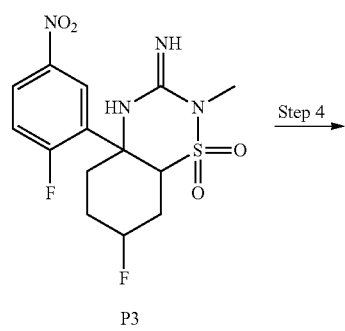
P3

Step 4 →

Step 1: Intermediate N13 is converted to intermediate P1 following a procedure similar to that described in Method J step 1.

Steps 2-4: Intermediate P1 is converted to P4 following procedures similar to those described in Method A steps 15-17 respectively.

Steps 5-6: Intermediate P4 is converted to Example 29 following procedures similar to those described in Method B steps 1-2 respectively.

| Ex | Structure IUPAC Name | LCMS m/z | BACE 1 $K_i$ (nM) | BACE2 $K_i$ (nM) |
|---|---|---|---|---|
| 29 | 5-fluoro-N-(4-fluoro-3-(7-fluoro-3-imino-2-methyl-1,1-dioxidohexahydro-2H-benzo[e][1,2,4]thiadiazin-4a(5H)-yl)phenyl)picolinamide | — | — | — |
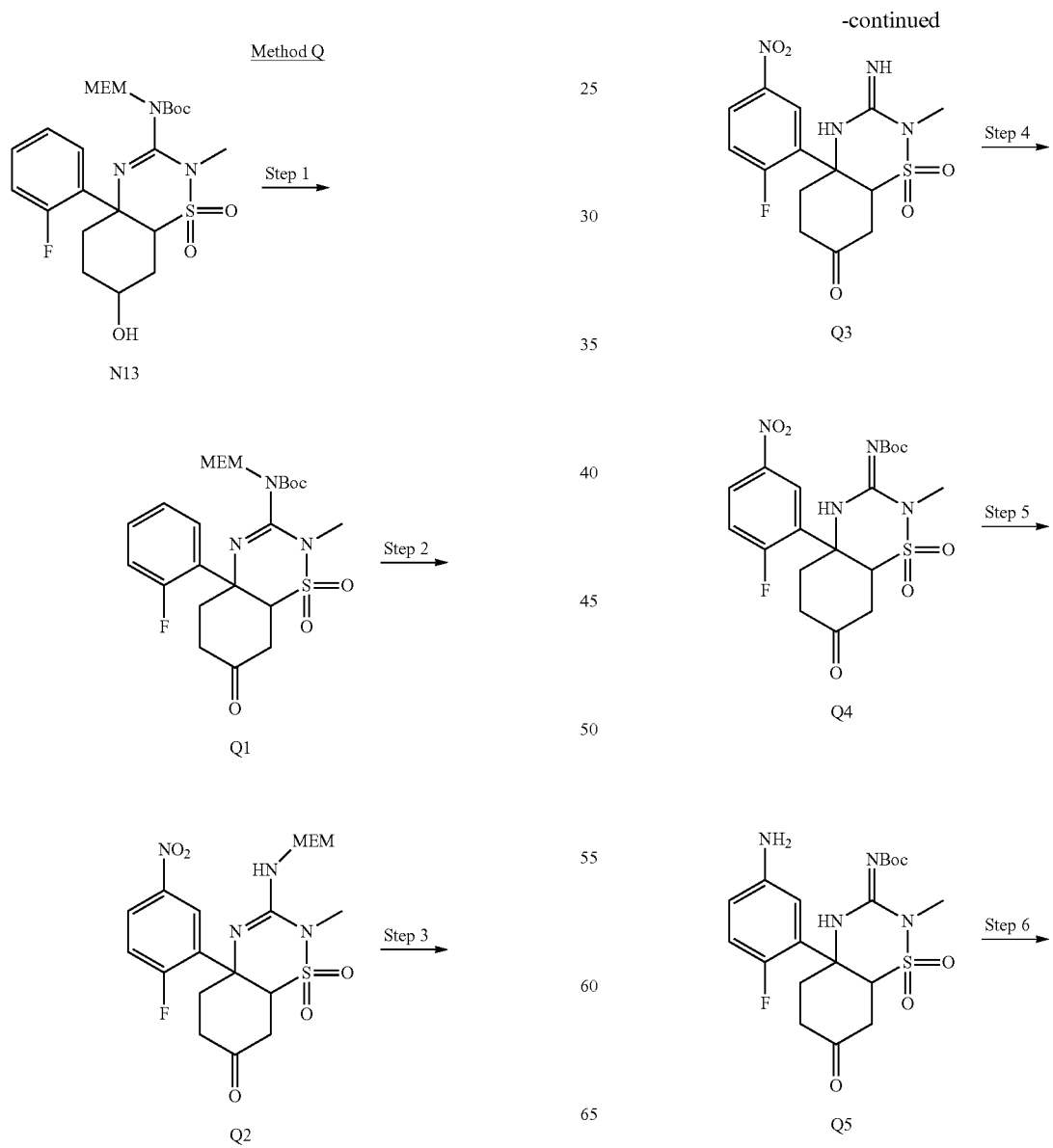
Method Q 79
-continued

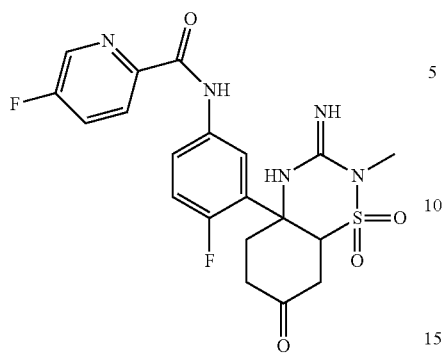

Example 30

Step 1 Intermediate N13 is converted to intermediate Q1 following a procedure similar to that described in Method K step 1.

Steps 2-4: Intermediate Q1 is converted to Q4 following procedures similar to those described in Method A steps 15-17 respectively.

Steps 5-6: Intermediate Q4 is converted to Example 30 following procedures similar to those described in Method B steps 1-2 respectively.

| Ex | Structure IUPAC Name | LCMS m/z | BACE1 $K_i$ (nM) | BACE2 $K_i$ (nM) |
|---|---|---|---|---|
| 30 | 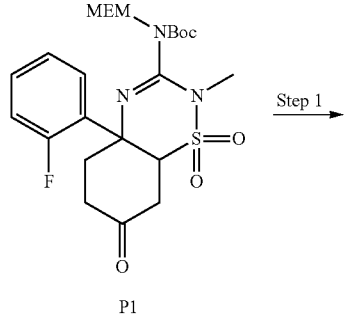 5-fluoro-N-(4-fluoro-3-(3-imino-2-methyl-1,1-dioxido-7-oxohexahydro-2H-benzo[e][1,2,4]thiadiazin-4a(5H)-yl)phenyl)picolinamide | — | — | — |

80
-continued

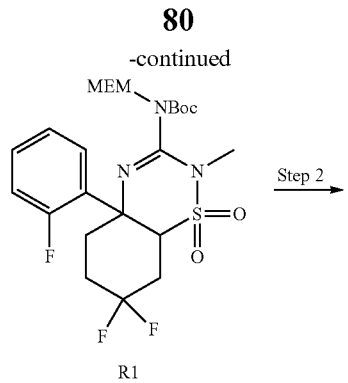

R1

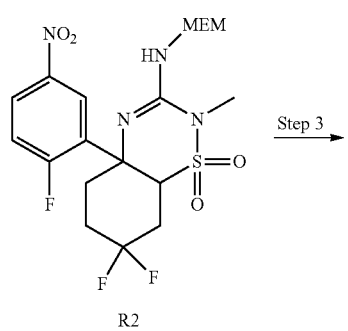

R2

Method R

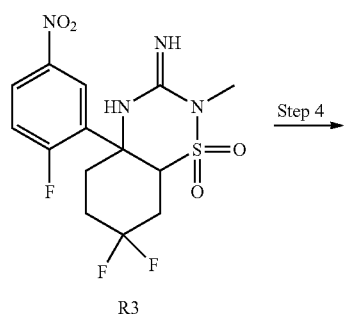

P1

-continued

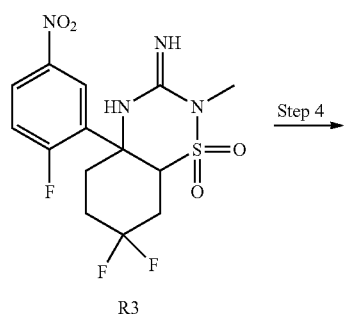

R3

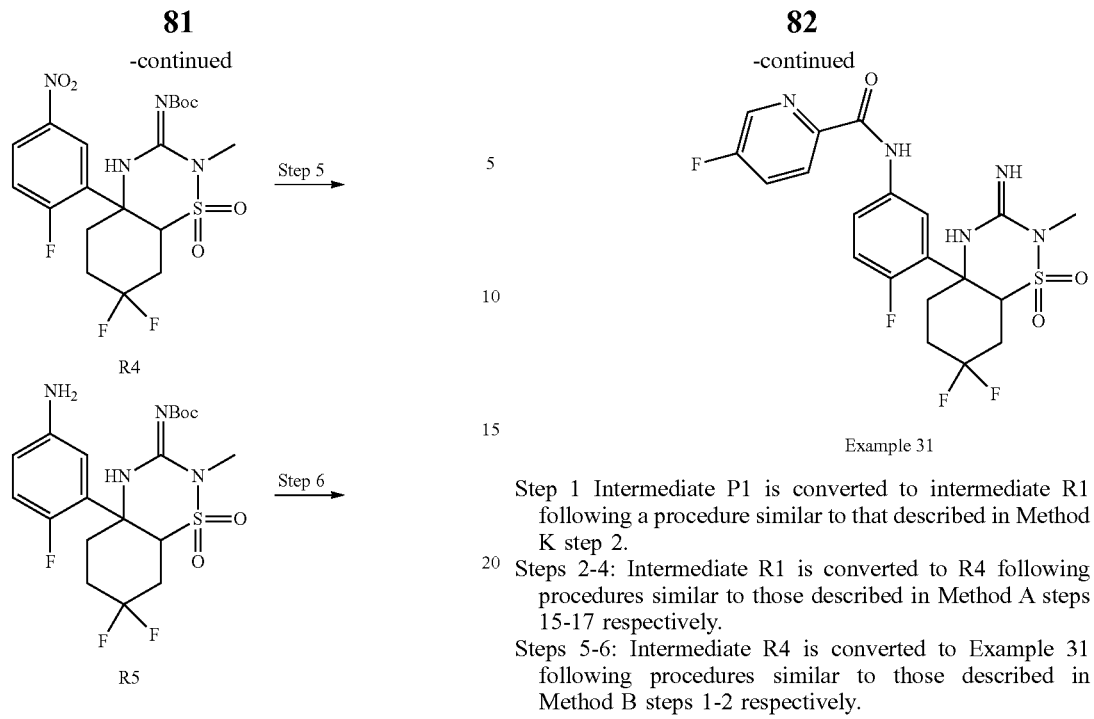

Step 1 Intermediate P1 is converted to intermediate R1 following a procedure similar to that described in Method K step 2.

Steps 2-4: Intermediate R1 is converted to R4 following procedures similar to those described in Method A steps 15-17 respectively.

Steps 5-6: Intermediate R4 is converted to Example 31 following procedures similar to those described in Method B steps 1-2 respectively.

| Ex | Structure IUPAC Name | LCMS m/z | BACE1 K$_i$ (nM) | BACE2 K$_i$ (nM) |
|---|---|---|---|---|
| 31 | 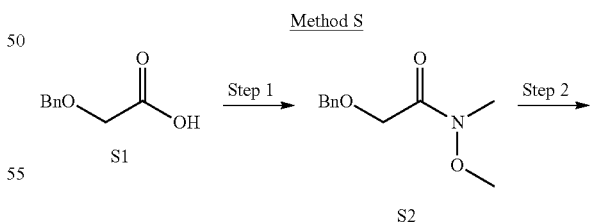 N-(3-(7,7-difluoro-3-imino-2-methyl-1,1-dioxidohexahydro-2H-benzo[e][1,2,4]thiadiazin-4a(5H)-yl)-4-fluorophenyl)-5-fluoropicolinamide | — | — | — |

Method S

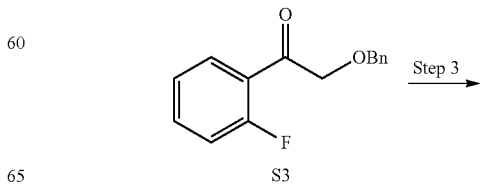

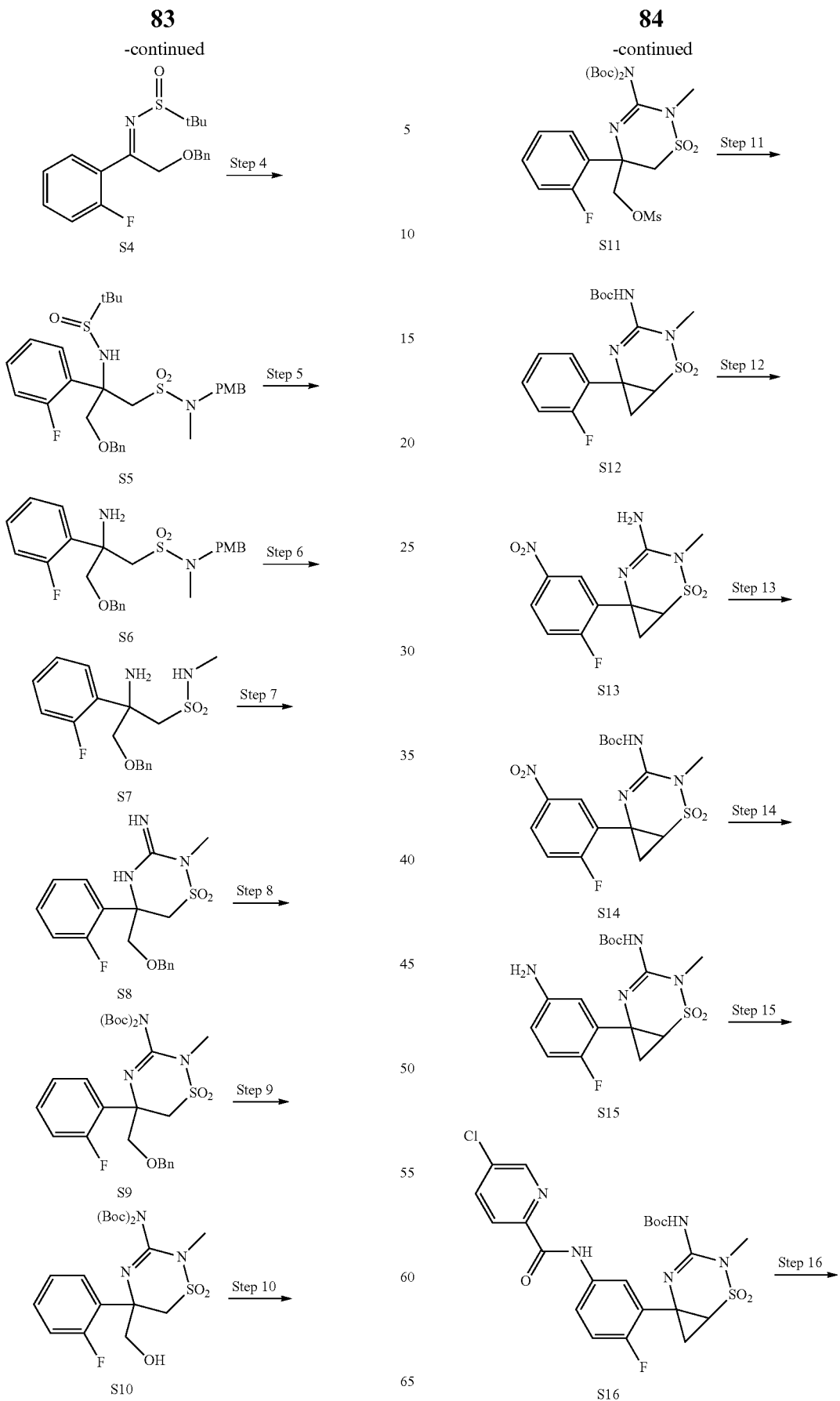

-continued

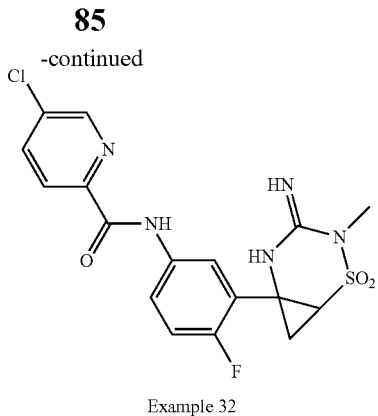

Example 32

Step 1. To a solution of S1 (3.23 g, 19.5 mmol) in DCM (60 mL) was added EDCI (6.1 g, 29.2 mmol), followed by N,O-dimethylhydroxylamine hydrochloride (2.8 g, 29.2 mmol) and pyridine (10 mL). The mixture was stirred at 25° C. for 16 h. After that time, the reaction mixture was washed with 0.1 M HCl and brine, dried over Na₂SO₄ and concentrated. The residue was purified by column chromatography eluting with PE:EtOAc (10:1) to afford compound S2. $^1$H NMR (CDCl₃, 400 MHz): 7.25-7.40 (m, 5H), 4.67 (s, 2H), 4.28 (s, 2H), 3.62 (s, 3H), 3.19 (s, 3H).

Step 2. To a suspension of magnesium (207 mg, 8.64 mmol) in THF (16 mL) was added one drop of 1,2-dibromoethane, followed by a solution of 1-bromo-2-fluorobenzene (756 mg, 4.32 mmol) in THF (8 mL) at 25° C. The mixture was stirred at 25° C. for 1 h and was then added to a solution of compound S2 (500 mg, 2.4 mmol) in THF (8 mL) at 0° C. The mixture was stirred at 0° C. for 1 h, quenched with saturated aq. NH₄Cl, and extracted with EtOAc. The combined extracts were washed with brine, dried over Na₂SO₄, concentrated and purified by column chromatography eluting with PE: EtOAc (30:1) to afford compound S3. $^1$H NMR (CDCl₃, 400 MHz): 7.93-7.97 (m, 1H), 7.50-7.55 (m, 1H), 7.23-7.40 (m, 6H), 7.08-7.13 (m, 1H), 4.70 (s, 2H), 4.69 (s, 2H).

Step 3. A mixture of compound S3 (5.8 g, 23.8 mmol), (R,S)-tert-butylsulfinamide (4.4 g, 35.7 mmol) and Ti(OEt)₄ (16.3 g, 71.4 mmol) in THF (60 mL) was stirred at 25° C. under N₂ for 16 h. After that time the mixture was diluted with ice-water and then filtered. The filtrate was extracted with EtOAc. The combined organic extracts were washed with water and brine then dried over Na₂SO₄ and concentrated. The residue was purified by column chromatography to afford compound S4. $^1$H NMR (CD₃OD, 400 MHz): 7.87-7.50 (m, 1H), 7.11-7.36 (m, 8H), 4.80 (s, 2H), 4.65 (s, 2H), 1.25 (s, 9H).

Step 4. To a solution of N-(4-methoxybenzyl)-N-methylmethanesulfonamide (2.64 g, 11.5 mmol) in THF (30 mL) at −78° C. was added n-BuLi (4.6 mL, 11.5 mmol, 2.5 M in hexane). The mixture was stirred at −78° C. for 1 h and a solution of compound S4 (2 g, 5.8 mmol) in THF (10 mL) was added. The resulting mixture was stirred at −78° C. for 3 h, quenched with saturated aq. NH₄Cl and extracted with EtOAc. The combined extracts were washed with brine, dried over Na₂SO₄, concentrated and purified by column chromatography (PE:EA=3:1) to afford compound S5. $^1$H NMR (CD₃OD, 400 MHz): 7.04-7.39 (m, 11H), 6.82-6.85 (m, 2H), 5.45-5.65 (m, 1H), 4.45-4.65 (m, 3H), 4.05-4.25 (m, 3H), 3.85-3.95 (m, 2H), 3.78 (s, 3H), 2.69 (s, 3H), 1.25 (s, 9H).

Step 5. To a solution of compound S5 (800 mg, 1.4 mmol) in DCM (10 mL) was added a solution of HCl in dioxane (2 mL, 4M) at 0° C. and the mixture was stirred at 25° C. for 1 h. The reaction mixture was then concentrated to afford compound S6 as HCl salt, which was used directly in next step without further purification.

Step 6. To a solution of compound S6 (706 mg, 1.4 mmol) in TFA (6 mL) at 0° C. was added thioglycolic acid (1.3 g, 14 mmol). The reaction mixture was stirred 25° C. for 16 h and then concentrated. The residue was basified with aq. NaHCO₃ solution to pH 8, and the mixture was then extracted with DCM. The combined organic extracts were washed with brine, dried over Na₂SO₄, concentrated and purified by column chromatography (PE:EA=2:1) to afford compound S7. $^1$H NMR (CD₃OD, 400 MHz): 7.59-7.63 (m, 1H), 7.19-7.37 (m, 7H), 7.03-7.08 (m, 1H), 4.47-4.54 (m, 2H), 3.80-3.84 (m, 2H), 3.68 (d, J=9.2 Hz, 1H), 3.56 (d, J=9.2 Hz, 1H), 2.52 (s, 3H).

Step 7. A solution of compound S7 (390 mg, 1.1 mmol) and BrCN (460 mg, 5.2 mmol) in CH₃CN (8 mL) was stirred at 60° C. for 16 h. The reaction mixture was concentrated and purified by column chromatography (0-3% MeOH in CH₂Cl₂) to afford compound S8. $^1$H NMR (CD₃OD, 400 MHz): 7.42-7.51 (m, 2H), 7.18-7.36 (m, 7H), 4.54-4.64 (m, 2H), 4.52 (d, J=14.2 Hz, 1H), 4.32 (d, J=14.2 Hz, 1H), 4.03 (d, J=10.0 Hz, 1H), 3.95 (d, J=10.0 Hz, 1H), 2.52 (s, 3H).

Step 8. A mixture of S8 (365 mg, 0.97 mmol), Boc₂O (627 mg, 2.9 mmol), DIPEA (374 mg, 2.9 mmol) and DMAP (50 mg, 0.3 mmol) in DCM (5 mL) was stirred at 30° C. for 16 h. The reaction mixture was concentrated and purified by column chromatography (PE:EA=10:1) to afford compound S9. $^1$H NMR (CDCl₃, 400 MHz): 7.59-7.64 (m, 1H), 7.26-7.32 (m, 6H), 7.06-7.13 (m, 1H), 7.00-7.04 (m, 1H), 4.60-4.63 (m, 1H), 4.52-4.55 (m, 1H), 4.12-4.16 (m, 1H), 3.89-3.93 (m, 2H), 3.77-3.80 (m, 1H), 3.11 (s, 3H), 1.49 (s, 18H).

Step 9. A solution of S9 (2.5 g, 0.0043 mol) in methanol (10 mL) was degassed by bubbling N₂. To this solution was added Pd(OH)₂ (50% w/w, 2.5 g). The atmosphere was evacuated and back-filled with hydrogen (pressure: 2 kg). The resulting mixture was stirred at 45° C. under hydrogen for 2 h. The mixture was then filtered through celite and the filter bed was washed with CH₂Cl₂/MeOH. The filtrate was then concentrated. The crude residue was purified by flash chromatography over silica gel using a gradient elution of 25% ethyl acetate in pet ether to yield S10. $^1$H NMR (CDCl3, 400 MHz): 7.54-7.49 (m, 1H), 7.36-7.29 (m, 1H), 7.15-7.04 (m, 2H), 4.13-3.95 (m, 3H), 3.77-3.74 (m, 1H), 3.17 (s, 3H), 2.82-2.79 (m, 1H), 1.58 (s, 18 H). LCMS m/z: 488.2 (M+1)⁺.

Step 10. To a solution of S10 (500 mg, 1.2 mmol) in CH₂Cl₂ (10 mL) was added triethylamine (0.7 mL, 5.1 mmol) and the mixture cooled to 0° C. Methanesulfonyl chloride (0.18 g, 0.0015 mol) was then added to the reaction and the mixture was stirred at 0° C. for 2 h. After that time, the reaction mixture was quenched with ice water and extracted with CH₂Cl₂. The organic layer was washed with a brine solution, dried over anhydrous Na₂SO₄, and concentrated under reduced pressure to provide S11 which was taken on to the next step without further purification. LCMS: m/z: 566.2 (M+1)⁺.

Step 11. To a solution of crude S11 (0.75 g, 1.3 mmol) in THF (20 mL) at −78° C. was added a solution of LiHMDS (3.9 mL, 3.9 mmol, 1.0 M solution in THF). The reaction mixture was stirred at −78° C. for 2 h. After that time, the reaction mixture was quenched with a saturated aq. NH₄Cl solution and the mixture was extracted with EtOAc. The combined organic layers were washed with brine, dried over anhydrous Na₂SO₄, and concentrated. The crude product was purified by flash silica gel chromatography eluting with 10% EtOAc in PE to afford S12. LCMS m/z: 370.2 (M-Boc)⁺.

Step 12. To S12 (70 mg) was added a cooled solution of 90% HNO₃ (2 mL) at −30° C. The resultant mixture was stirred at −30° C. for 4 h and then slowly poured onto ice. The mixture was basified with solid NaHCO₃ (to pH 8). The mixture was then extracted with EtOAc. The combined organic layers were dried over anhydrous Na₂SO₄ and concentrated to yield crude S13 was as such taken on to the next step without further purification. LCMS: m/z: 315.0 (M+1)⁺.

Step 13. To a solution of S13 (70 mg, 0.22 mmol) at 0° C. in dichloromethane (5 mL) was added DIPEA (0.19 mL, 1.1 mmol) and Boc₂O (145 mg, 0.66 mmol). The reaction mixture was warmed to RT and stirred for 16 h. The reaction mixture was then concentrated and the crude residue was purified by flash silica gel chromatography eluting with 10% EtOAc in PE to afford S14. LCMS m/z 415.2 (M+1)⁺.

Step 14. A solution of S14 (50 mg, 0.12 mmol) in methanol (5 mL) was degassed by bubbling N₂ through it. To this solution was added Pd/C (10% w/w, 20 mg.). The mixture was then placed under an atmosphere of N₂. The atmosphere was evacuated and back-filled with hydrogen. The resulting mixture was stirred at RT under an atmosphere of hydrogen for 4 h. The mixture was purged with nitrogen then filtered through celite and the celite bed was washed with excess CH₂Cl₂/MeOH mixture and concentrated. The crude S15 was taken on to the next step without further purification. LCMS m/z: 385.2 (M+1)⁺.

Step 15. To a solution of S15 (100 mg, 0.26 mmol) in THF (5 mL) at 0° C. was added 5-chloropyridine-2-carboxylic acid (61 mg, 0.39 mmol), DIPEA (0.23 mL, 1.3 mmol), and a solution of 1-propanephosphonic acid cyclic anhydride in (50% in EtOAc, 0.24 g, 0.78 mmol) respectively. The reaction mixture was then stirred for 2 h at RT. After that time, water was added to the reaction and the mixture was extracted with EtOAc. The combined organic layers were washed with water and brine, dried over anhydrous Na₂SO₄ and concentrated. The crude residue was purified by flash silica gel chromatography eluting with 40% ethyl acetate in PE to afford S16. LCMS; purity: m/z: 524.2 (M+1)⁺.

Step 16: To a solution of S16 (20 mg) in dichloromethane (2 mL) at 0° C. was added TFA (1 mL). The reaction was stirred for 2 h at RT and then concentrated in vacuo. The residue was washed with diethyl ether to yield Example 32. ¹H NMR (400 MHz, CD₃OD): δ 8.72 (d, J=2.36 Hz, 1H), 8.22 (d, J=8.44 Hz, 1H), 8.11-8.04 (m, 2H), 7.89-7.85 (m, 1H), 7.29 (t, J=9.2 Hz, 1H), 4.05-4.02 (m, 1H), 3.45 (s, 3H), 2.41-2.37 (m, 1H), 2.22-2.18 (m, 1H). LCMS m/z: 424.2 (M+1)⁺.

| Ex | Structure IUPAC Name | LCMS m/z | BACE1 $K_i$ (nM) | BACE2 $K_i$ (nM) |
|---|---|---|---|---|
| 32 | | 424.2 | 2516 | 1157 |

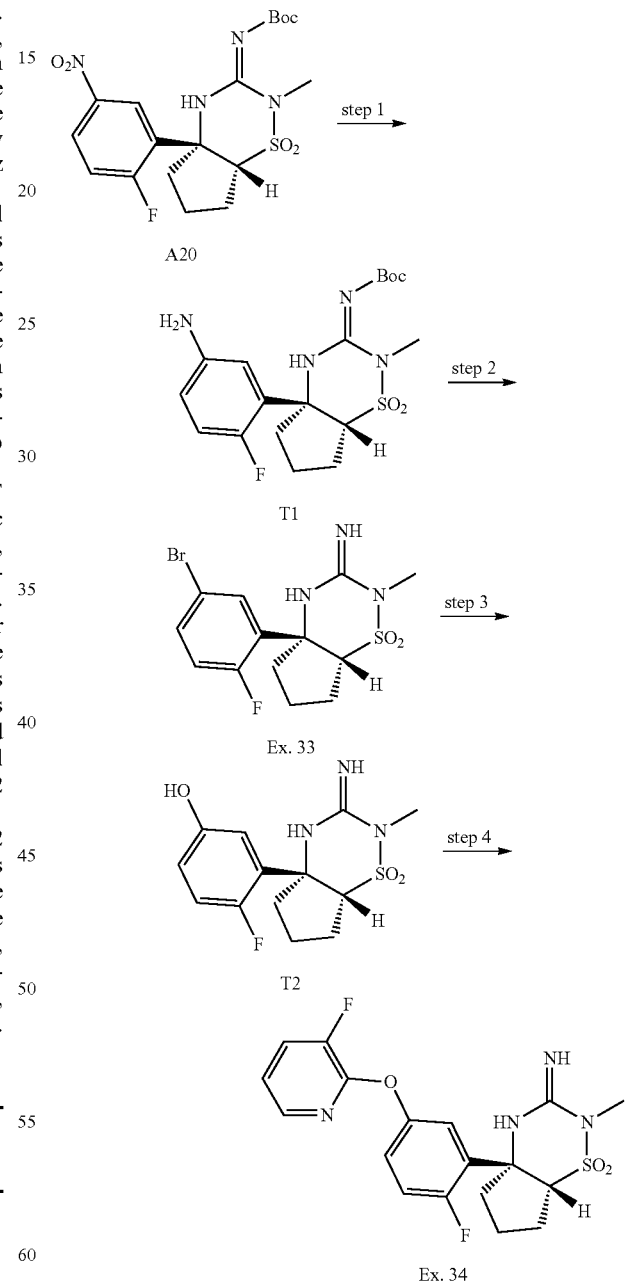

5-chloro-N-(4-fluoro-3-(4-imino-3-methyl-2,2-dioxido-2-thia-3,5-diazabicyclo[4.1.0]heptan-6-yl)phenyl)picolinamide Method T Step 1. To a pressure vial equipped with a stir bar was added A20 (400 mg, 0.904 mmol) followed by THF (4.5 mL). To the mixture was added potassium fluoride (105 mg, 1.81 mmol). The mixture was purged with N₂ for 1 min. To the mixture was then added palladium acetate (10.1 mg, 0.0450 mmol) followed by 1,3-bis(trimethylsiloxy)-1,3-dimethyldisiloxane (256 μl, 0.904 mmol). The mixture was stirred at RT for 18 hour, then filtered through Celite and diluted with water. The layers were separated and the aqueous layer was extracted with EtOAc (3×). The combined organic layers were washed with brine, dried (sodium sulfate), filtered and concentrated. The crude product was purified via flash chromatography to afford T1. MS for T1: m/e=413.3 (M+1).

Step 2. T1 (162 mg, 0.393 mmol) was dissolved in a mixture of 48% HBr (1.0 ml) and Water (2.0 ml) and cooled to 0° C. Sodium nitrite (32.5 mg, 0.471 mmol) was dissolved in water (2.0 ml) and added dropwise. In a separate flask, CuBr (73.2 mg, 0.511 mmol) was taken up in a mixture of 48% HBr (1.0 ml) and water (2.0 ml) and cooled to 0° C. The diazonium salt solution was added dropwise to the CuBr solution under vigorous stirring. The mixture was allowed to warm to room temperature and subsequently heated to 70° C. for 1 h. The resulting suspension was cooled to room temperature, diluted with water, and extracted with DCM (2×). The combined organic layers were washed with brine, dried (MgSO$_4$), and concentrated. The crude product was purified via flash chromatography to afford Example 33. MS for Example 33: m/e=378.2 and 376.2 (M+1).

Step 3. To a vial containing Example 33 (81.0 mg, 0.215 mmol) was added Ad-BrettPhos G3 precatalyst (21.8 mg, 0.0220 mmol) followed by DMSO (0.5 ml) and water (0.019 ml, 1.08 mmol). The mixture was purged with a stream of dry N$_2$ followed by addition of P2-Et phosphazene base (Aldrich) (0.215 ml, 0.646 mmol). The mixture was stirred at RT for 4 hours then partitioned between EtOAc and sat NH4Cl (aq.). The aqueous layer was extracted with EtOAc and the combined organic layers were washed successively with water (2×) and brine, then dried, filtered and concentrated. The crude product was purified via flash chromatography to afford T2. MS for T2: m/e=314.3 (M+1).

Step 4. A solution of T2 (0.014 g, 0.045 mmol) in DMF (0.5 mL) was treated at rt with sodium hydride (5.34 mg, 0.134 mmol). After stirring 30 min., 2,3-difluoropyridine (7.71 mg, 0.067 mmol) was added and the mixture was heated at 50° C. in the MW for 45 min. The resulting reaction mixture was colled and filtered, then diluted with water and extracted with EtOAc (2×). The combined organic layers were washed with brine, dried (Na$_2$SO$_4$), filtered and concentrated. The resulting residue was purified by flash chromatography to afford Example 34. $^1$H NMR (400 MHz, CD$_3$OD): δ 7.46 (m, 1H), 7.22 (m, 1H), 7.05-6.97 (m, 2H), 6.80 (m, 1H), 6.42 (m, 1H), 3.34 (m, 1H), 3.45 (s, 3H), 2.15-1.88 (m, 4H), 1.67-1.61 (m, 2H). LCMS m/z: 409.3 (M+1)$^+$.

| Ex | Structure IUPAC Name | LCMS m/z | BACE-1 Inh. @ 10 μM | BACE-2 Inh. @ 10 μM |
|---|---|---|---|---|
| 33 | 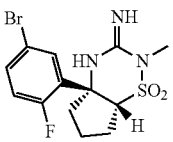 (4aR,7aR)-4a-(5-bromo-2-fluorophenyl)-3-imino-2-methyloctahydrocyclopenta | 378.2/ 376.2 | 18% | 18% |

[e][1,2,4]thiadiazine 1,1-dioxide

| Ex | Structure IUPAC Name | LCMS m/z | BACE-1 Ki (nM) | BACE-2 Ki (nM) |
|---|---|---|---|---|
| 34 | 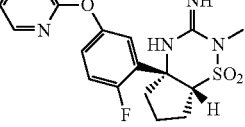 (4aR,7aR)-4a-(2-fluoro-5-((3-fluoropyridin-2-yl)oxy)phenyl)-3-imino-2-methyloctahydrocyclopenta[e][1,2,4]thiadiazine 1,1-dioxide | 409.3 | 89 | 75 |

Method U

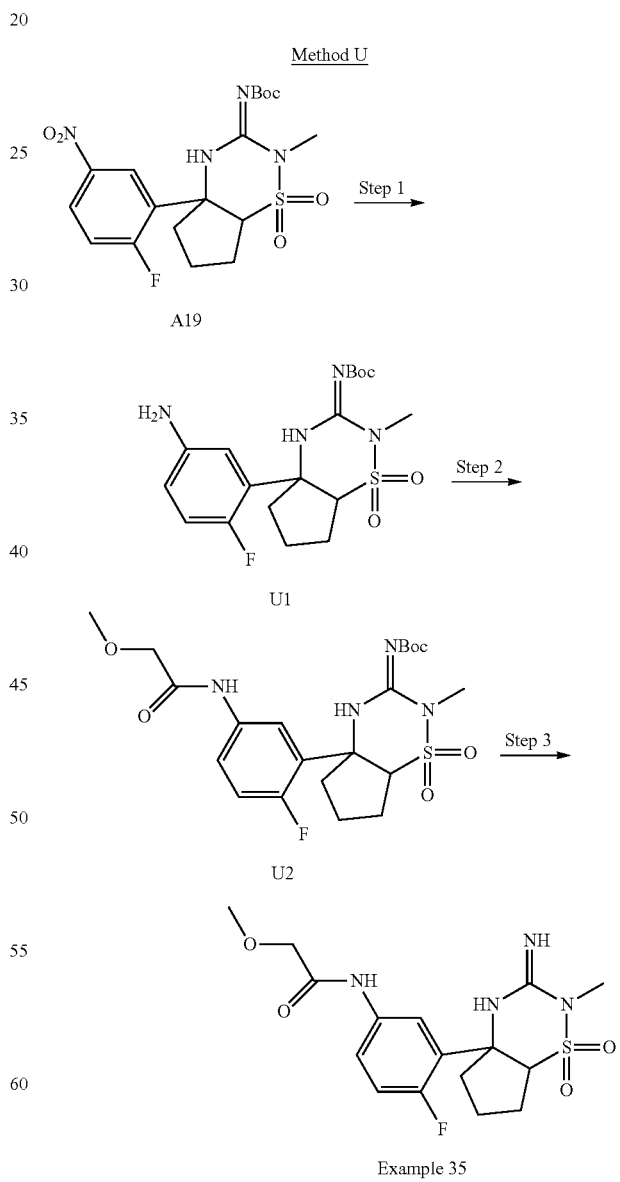

Example 35

Step 1. A solution of A19 (50 mg, 0.13 mmol) in methanol (10 mL) was degassed by bubbling N$_2$ gas through it. To this solution was added Pd/C (10% w/w, 10 mg.). The reaction vessel was then evacuated and back-filled with hydrogen. The resulting mixture was stirred at RT under an atmosphere of hydrogen for 3 h. After that time, the mixture was filtered through celite and the celite bed was washed with a dichloromethane/MeOH mixture and the filtrate was concentrated. The crude product U1 was taken for next step without further purification. LCMS m/z: 413.4 (M+H)+.

Step 2. To a mixture of U1 (50 mg, 0.12 mmol) in THF (5 mL) at 0° C. was added methoxy acetic acid (16 mg, 0.18 mmol), N,N-diisopropylethylamine (0.1 mL, 0.61 mmol), and a solution of 1-propanephosphonic acid cyclic anhydride in (50% in EtOAc, 0.116 g, 0.37 mmol). The reaction mixture was then stirred for 3 h at RT. After that time, water was added to the reaction and the mixture was extracted with EtOAc. The combined organic layers were washed with water and brine, then dried over $Na_2SO_4$ and concentrated. The crude residue was purified by flash silica gel chromatography eluting with 20% EtOAc in PE to afford U2. LCMS m/z: 485.4 (M+H)+.

Step 3. To a solution of U2 (50 mg) in dichloromethane (2 mL) at 0° C. was added TFA (2 mL). The reaction mixture was stirred for 2 h at RT and then concentrated in vacuo. The residue was washed with diethyl ether to afford Example 35. $^1$H-NMR (CD$_3$OD, 400 MHz): δ. 7.98 (dd, J=2.60, 7.56 Hz, 1H), 7.64-7.60 (m, 1H), 7.26-7.21 (m, 1H), 4.60 (t, J=7.32 Hz, 1H), 4.06 (s, 2H), 3.50 (s, 3H), 3.41 (s, 3H), 2.82-2.75 (m, 1H), 2.50-2.40 (m, 3H), 2.13-2.06 (m, 2H).

LCMS m/z: 385.2 (M+H)+.

Example 36 was prepared from U1 following procedures similar to those described in Method U steps 2 and 3 using difluoroacetic acid instead of methoxy acetic acid in step 2.

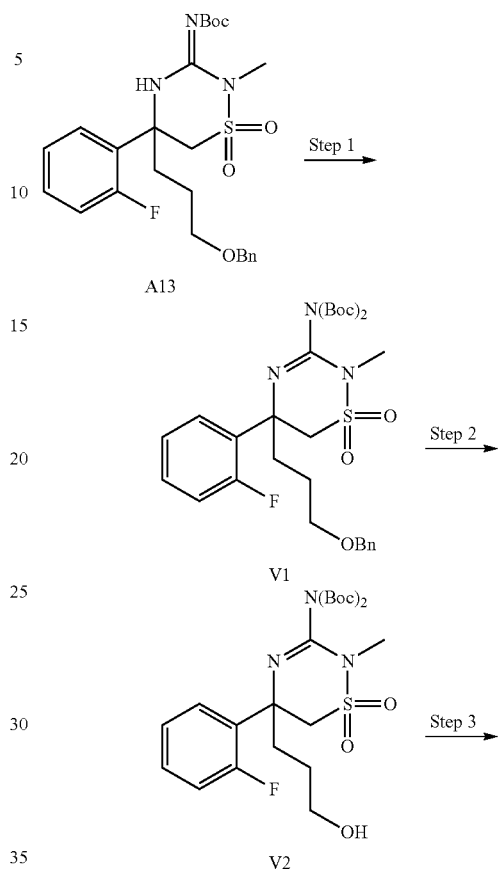

Method V

| Ex | Structure<br>IUPAC Name | LCMS m/z | BACE-1 $K_i$ (nM) | BACE-2 $K_i$ (nM) |
|---|---|---|---|---|
| 35 | 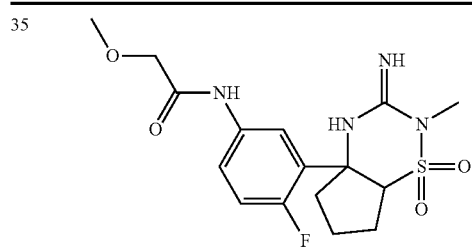<br>N-(4-fluoro-3-(3-imino-2-methyl-1,1-dioxidohexahydrocyclopenta[e][1,2,4]thiadiazin-4a(2H)-yl)phenyl)-2-methoxy acetamide | 385.2 | 368 | 16 |
| 36 | 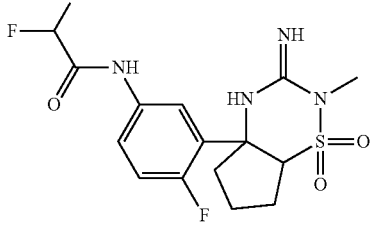<br>2,2-difluoro-N-(4-fluoro-3-(3-imino-2-methyl-1,1-dioxidohexahydrocyclopenta[e][1,2,4]thiadiazin-4a(2H)-yl)phenyl)acetamide | 391.2 | 1084 | 71 |

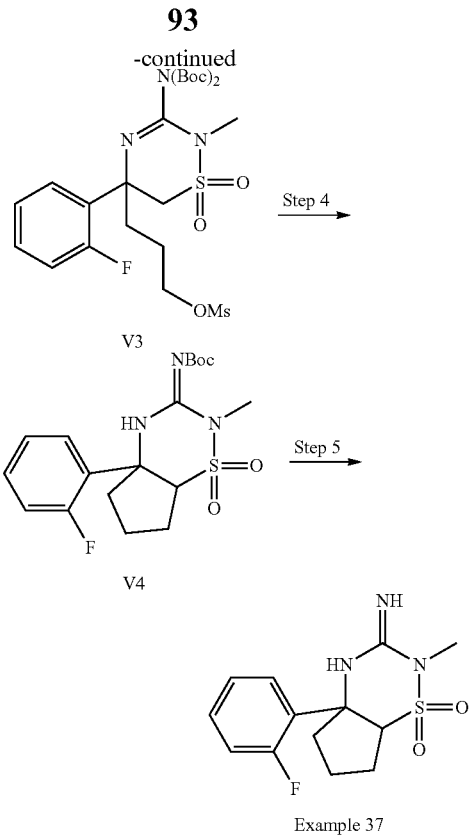

extracts were washed with brine, dried over anhydrous Na$_2$SO$_4$, concentrated and purified by flash silica gel chromatography eluting with 10% EtOAc in PE as eluent to afford V4. LCMS m/z: 398.4 (M+H)$^+$.

Step 5. Intermediate V4 was converted to Example 37 using a procedure similar to that described in Method U step 3.

| Ex | Structure IUPAC Name | LCMS m/z | BACE-1 Inh. @ 10 μM | BACE-2 K$_i$ (nM) |
|---|---|---|---|---|
| 37 | 4a-(2-fluorophenyl)-3-imino-2-methyloctahydrocyclopenta[e][1,2,4]thiadiazine 1,1-dioxide | 298.0 | 43% | 4087 |

Biological Assays

Protocols that may be used to determine the recited biological properties for the compounds of the invention are described below.

Assay 1: BACE-1 Ki Assay (BACE-1 HTRF FRET Assay)

The compounds of the invention were assessed for their ability to inhibit BACE-1 using the following assay. The resulting values are reported in the tables above.

The following reagents were used in this assay. Na$^+$-Acetate pH 5.0; 1% Brij-35; Glycerol; Dimethyl Sulfoxide (DMSO); Recombinant human soluble BACE-1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine IC$_{50}$ values for inhibitors of the soluble human BACE-1 catalytic domain. This assay monitors the increase of 620 nm fluorescence that resulted from BACE-1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE-1 enzyme. Inhibition of BACE-1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE-1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions are initiated by addition of 10 μl of 600 nM QSY7-APP$^{swe}$-Eu substrate (200 nM final) to give a final reaction volume of 30 μl in a 384 well Nunc HTRF plate. The reactions are incubated at 30° C. for 1.5 hours. The 620 nm fluorescence is then read on a Rubystar HTRF plate reader (BMG Labtechnologies) using a 50 milisecond delay followed by a 400 milisecond acquisition time window. Inhibitor IC$_{50}$ values are derived from non-linear regression analysis of concentration response curves. Ki values are then calculated from IC$_{50}$ values using the Cheng- Step 1. To a solution of A3 (0.7 g, 1.4 mmol) in dichloromethane (10 mL) at 0° C. was added DIPEA (1.2 mL, 6.9 mmol), DMAP (84 mg, 0.69 mmol), and Boc$_2$O (0.9 g, 4.9 mmol). The reaction mixture was allowed to warm to RT and stir for 16 h. After that time, the reaction mixture was concentrated and the crude residue was purified by flash silica gel chromatography eluting with 15% EtOAc in PE to afford V1. LCMS m/z 606.4 (M+H)$^+$.

Step 2. A solution of V1 (0.7 g, 1.2 mol) in methanol (10 mL) was degassed by bubbling N$_2$ gas through it. To this solution was added Pd(OH)$_2$/C (50% w/w, 0.7 g.). The atmosphere was evacuated and back-filled with hydrogen to 2 kg pressure. The resulting mixture was stirred at 45° C. for 2 h. The mixture was then purged with nitrogen and filtered through celite. The celite bed was washed with a mixture of dichloromethane/MeOH and the filtrate was concentrated to afford V2 that was carried on without further purification. LCMS m/z: 516.4 (M+H)$^+$.

Step 3. To a solution of V2 (300 mg, 0.58 mmol) in dichloromethane (10 mL) was added triethylamine (0.4 mL, 2.9 mmol) and the mixture was cooled to 0° C. To the reaction mixture was added methanesulfonyl chloride (0.099 g, 0.87 mmol) and the reaction mixture was stirred at 0° C. for 2 h. The reaction mixture was then quenched with ice water and extracted with dichloromethane. The organic layer was washed with a saturated brine solution, dried over anhydrous Na$_2$SO$_4$, and concentrated under reduced pressure to afford V3 which was carried on to the next step without further purification.

Step 4. To a solution of crude V3 (0.4 g, 0.67 mmol) in THF (10 mL) at 0° C. was added KOtBu (0.37 g, 3.4 mmol). The reaction mixture was stirred at 0° C. for 3 h. After that time, the reaction mixture was quenched with ice and the mixture was extracted with EtOAc. The combined Prusoff equation using a previously determined μm value of 8 μM for the QSY7-APP$^{swe}$-Eu substrate at BACE-1. The example compounds of the invention were measured in this assay. Their measured Ki values are reported in the tables above.

Assay 2: BACE-2 Assay

The compounds of the invention were assessed for their ability to inhibit BACE-1 using the following assay. The resulting values are reported in the tables above.

Inhibitor IC$_{50s}$ at purified human autoBACE-2 were determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1×BACE assay buffer (final enzyme concentration 1 nM) in black 384-well NUNC plates for 30 minutes at 30° C. The assay was initiated by addition of an equal volume of the QSY7-EISEVNLDAEFC-Eu-amide substrate (200 nM final concentration, K$_m$=8 μM for 4 μM for autoBACE-2) prepared in 1× BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm was collected for 400 ms following a 50 s delay on a RUBYstar HTRF plate reader (BMG Labtechnologies). Raw RFU data was normalized to maximum (1.0 nM BACE/DMSO) and minimum (no enzyme/DMSO) RFU values. IC$_{50}$ values were determined by nonlinear regression analysis (sigmoidal dose response, variable slope) of percent inhibition data with minimum and maximum values set to 0 and 100 percent respectively. Similar IC$_{50s}$ were obtained when using raw RFU data. The K$_i$ values were calculated from the IC$_{50}$ using the Cheng-Prusoff equation.

While the present invention has been described in view of the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or a pharmaceutically acceptable salt thereof, said compound having the structural Formula (I):

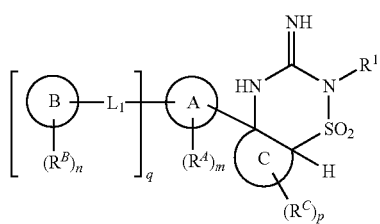

or a tautomer thereof having the structural Formula (I'):

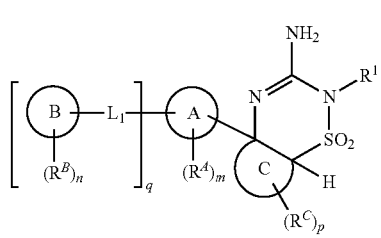

or pharmaceutically acceptable salt thereof, wherein:
ring C is a 3-, 4-, 5-, or 6-membered fused cycloalkyl group;
p is 1, 2, 3, or 4, provided that the value of p does not exceed the number of substitutable hydrogen atoms on ring C;
each R$^C$ is independently selected from the group consisting of H, F, —OH, oxo, lower alkyl, lower cycloalkyl, —O-(lower alkyl) and —O-(lower cycloalkyl),
 wherein each said lower alkyl and lower cycloalkyl are optionally substituted with one or more fluorine, and
 wherein 1 to 2 non-adjacent, non-terminal carbon atoms in each said lower alkyl are optionally independently replaced with —O—, —NH—, —N-(lower alkyl)-, —S—, —S(O)—, or —S(O)$_2$—;
R$^1$ is selected from the group consisting of H, lower alkyl, lower cycloalkyl, and -(lower alkyl)-(lower cycloalkyl),
 wherein each said lower alkyl and lower cycloalkyl are optionally substituted with one or more fluorine, and
 wherein 1 to 2 non-adjacent, non-terminal carbon atoms in each said lower alkyl are optionally independently replaced with —O—, —NH—, —N-(lower alkyl)-, —S—, —S(O)—, or —S(O)$_2$—;
ring A is selected from the group consisting of aryl and heteroaryl;
m is 0, 1, 2, or 3, provided that the value of m does not exceed the number of substitutable hydrogen atoms on ring A;
each R$^A$ (when present) is independently selected from the group consisting of halogen, —CN, —OH, oxo, —NH-(lower alkyl), —NHC(O)-(lower alkyl), lower alkyl, -(lower alkyl)-(lower cycloalkyl), and —O-(lower alkyl),
 wherein each said lower alkyl and lower cycloalkyl are optionally substituted with one or more fluorine, and
 wherein 1 to 2 non-adjacent, non-terminal carbon atoms in each said lower alkyl are optionally independently replaced with —O—, —NH—, —N-(lower alkyl), —S—, —S(O)—, or —S(O)$_2$—;
q is 0 or 1;
-L$_1$-, when present, represents a bond or a divalent moiety selected from the group consisting of —C(O)NH—, —CH$_2$C(O)NH—, —NH—, —CH(CH$_3$)NH—, —CH$_2$NH—, —O—, and —CH$_2$O—;
ring B, when present, is selected from the group consisting of aryl, heteroaryl, cycloalkyl, and heterocycloalkyl;
n is 0, 1, 2, or 3, provided that the value of n does not exceed the number of substitutable hydrogen atoms on ring B; and
each R$^B$, when present, is independently selected from the group consisting of halogen, —CN, —OH, oxo, lower alkyl, lower cycloalkyl, -(lower alkyl)-(lower cycloalkyl), —O-(lower alkyl), —O-(lower cycloalkyl), —O-(lower alkyl)-(lower cycloalkyl), —C≡CH, —C≡C—CH₃, —OCH₂—C≡C—H, and —OCH₂—C≡C—CH₃, wherein each said lower alkyl and lower cycloalkyl are optionally substituted with one or more fluorine, and wherein 1 to 2 non-adjacent, non-terminal carbon atoms in each said lower alkyl are optionally independently replaced with —O—, —NH—, —N-(lower alkyl)-, —S—, —S(O)—, or —S(O)₂—.

2. A compound of claim 1, or a pharmaceutically acceptable salt thereof, said compound having the structural Formula (II):

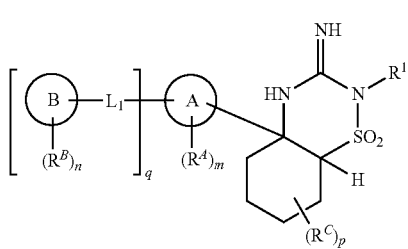

or a tautomer thereof having the structural Formula (II'):

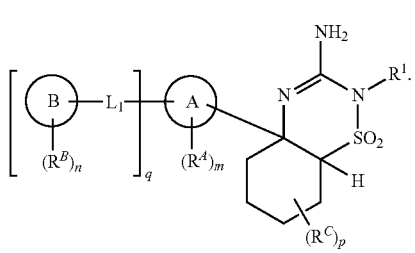

3. A compound of claim 1, or a pharmaceutically acceptable salt thereof, said compound having the structural Formula (III):

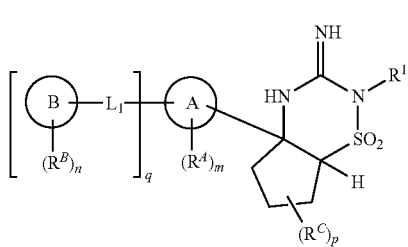

or a tautomer thereof having the structural Formula (III'):

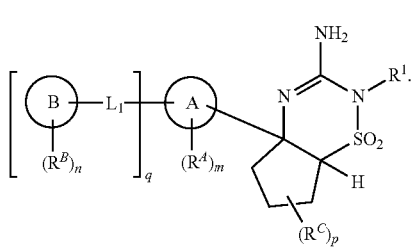

4. A compound of claim 1, or a pharmaceutically acceptable salt thereof, said compound having the structural Formula (IV):

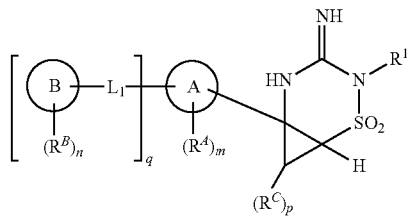

or a tautomer thereof having the structural Formula (IV'):

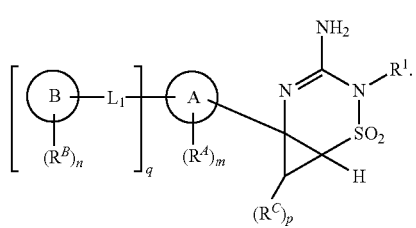

5. A compound of any of claims 1 to 4, or a tautomer thereof, or a pharmaceutically acceptable salt of said compound or said tautomer, wherein:

p is 1 or 2, provided that the value of p does not exceed total number of valences on ring C; and each $R^C$ is independently selected from the group consisting of H, F, —OCH₃, and oxo.

6. A compound of claim 1, or a tautomer thereof, or a pharmaceutically acceptable salt of said compound or said tautomer, wherein:

$R^1$ is methyl.

7. A compound of claim 1, or a tautomer thereof, or a pharmaceutically acceptable salt of said compound or said tautomer, wherein:

q =1;
-L₁- is —C(O)NH—;
ring A is selected from the group consisting of phenyl and pyridinyl;
m is 0, 1, 2, or 3;
each $R^A$, when present, is independently selected from the group consisting of fluoro, chloro, methyl, and —CHF₂.
ring B is selected from the group consisting of phenyl, pyridinyl, pyrazinyl, pyrimidinyl, and pyridazinyl;
n is 0, 1, 2, or 3; and
each $R^B$ (when present) is independently selected from the group consisting of fluoro, chloro, bromo, —CN, —OH, methyl, ethyl, cyclopropyl, —CH₂OCH₃, —C≡CH, —C≡C—CH₃, —CF₃, —CHF₂, —CH₂F, —OCH₂—C≡C—H, —OCH₂—C≡C—CH₃, —OCH₃, —OCF₃, —OCHF₂, —OCH₂F, —OCH₂CF₃, —OCH₂CHF₂, and —OCH₂CH₂F.

8. A compound of claim 1, or a tautomer thereof, or a pharmaceutically acceptable salt of said compound or said tautomer, wherein:

q =1;
-L₁- is —NH—;
ring A is selected from the group consisting of phenyl and pyridinyl;
m is 0, 1, 2, or 3;
each $R^A$ (when present) is independently selected from the group consisting of fluoro, chloro, methyl, and —CHF₂;

ring B is selected from the group consisting of pyridinyl, pyrazinyl, dihydrocyclopentapyridinyl, dihydroindenyl, naphthyridinyl, pteridinyl, pyridopyrazinyl, pyridopyrimidinyl, and tetrahydroquinolinyl;

n is 0, 1, 2, or 3; and each $R^B$ (when present) is independently selected from the group consisting of fluoro, chloro, bromo, —CN, —CF$_3$, —CHF$_2$, —OCH$_3$, —OCF$_3$, —OCHF$_2$, —OCH$_2$CF$_3$, and —OCH$_2$CHF$_2$.

9. A compound of claim 1, or a tautomer thereof, or a pharmaceutically acceptable salt of said compound or said tautomer, wherein:

q =1;

-L$_1$- is —O—;

ring A is selected from the group consisting of phenyl and pyridinyl;

m is 0, 1, 2, or 3;

each $R^A$ (when present) is independently selected from the group consisting of fluoro, chloro, methyl, and —CHF$_2$;

ring B is selected from the group consisting of pyrazinyl, pyridinyl, and pyrimidinyl;

n is 0, 1, or 2; and each $R^B$ group (when present) is independently selected from the group consisting of fluoro, —CN, —CF$_3$ and —OMe.

10. A compound of claim 1, or a tautomer thereof, or a pharmaceutically acceptable salt of said compound or said tautomer, wherein:

q =0;

ring A is selected from the group consisting of phenyl, pyridazinyl, pyridinyl, pyrimidinyl, pyrazinyl, pyrazolyl, triazinyl, thiazolyl, and thienyl;

m is 0, 1, 2, 3, or 4, provided that the value of m does not exceed the number of available substitutable hydrogen atoms on ring A; and each $R^A$ (when present) is independently selected from the group consisting of fluoro, chloro, bromo, oxo, —OH, —CN, methyl, ethyl, propyl, butyl, —CH$_2$OCH$_3$, —CH$_2$OCF$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$NHCH$_2$CF$_3$, —CF$_3$, —CHF$_2$, —CH$_2$F, —NH$_2$, —NH$_2$CH$_2$CF$_3$, —NHC(O)CH$_3$, —NHC(O)CHF$_2$, —NHC(O)CH$_2$OCH$_3$, —OCH$_3$, —OCH$_2$CH$_3$, —OCH$_2$CH$_2$CH$_3$, —OCH$_2$CH(CH$_3$)$_2$, —OCH$_2$CH$_2$OCH$_3$, —OCF$_3$, —OCHF$_2$, —OCH$_2$F, —OCH$_2$CF$_3$, —OCH$_2$CHF$_2$, —OCH$_2$CH$_2$F, and —OCH$_2$CH$_2$CF$_3$.

11. A compound of claim 1, or a tautomer thereof, or a pharmaceutically acceptable salt of said compound or said tautomer, said compound selected from the group consisting of:

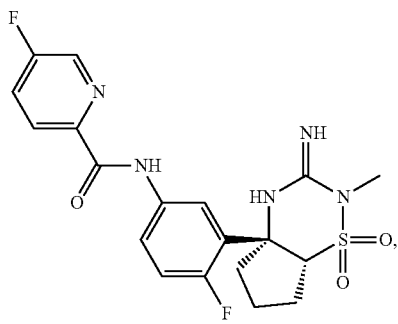

-continued

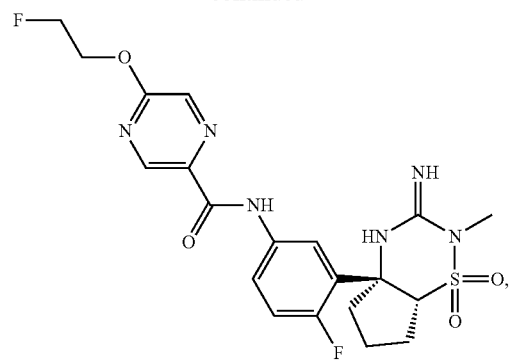

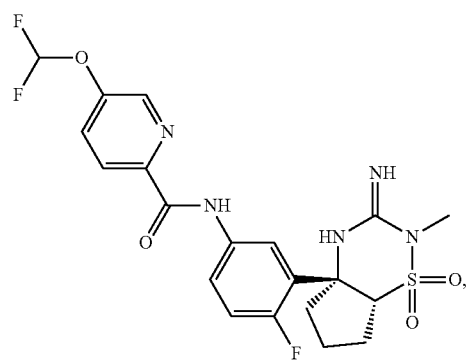

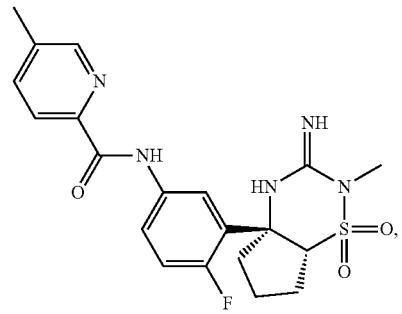

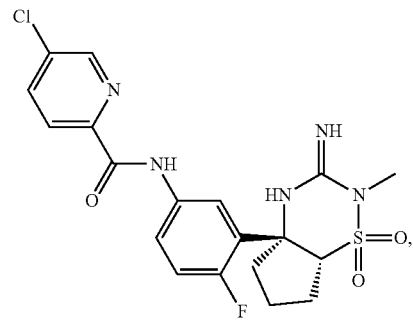 [SMILES: CN1C(=N)N[C@@]2(c3cc(NC(=O)c4ccc(Cl)cn4)ccc3F)CCC[C@H]2S1(=O)=O]

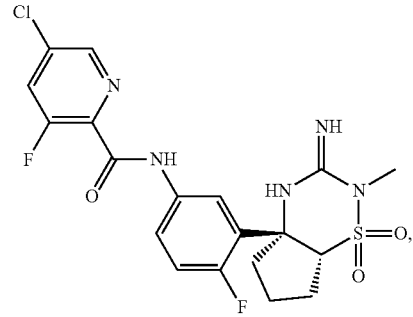 [SMILES: CN1C(=N)N[C@@]2(c3cc(NC(=O)c4ncc(Cl)cc4F)ccc3F)CCC[C@H]2S1(=O)=O]

-continued
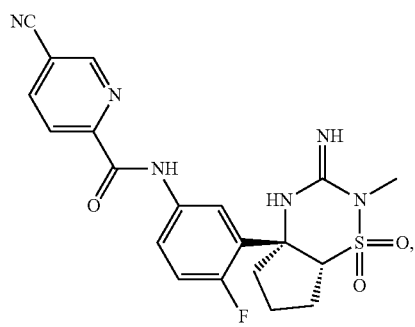
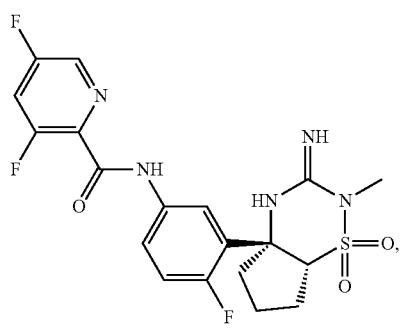
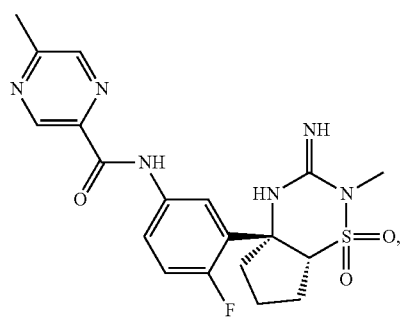
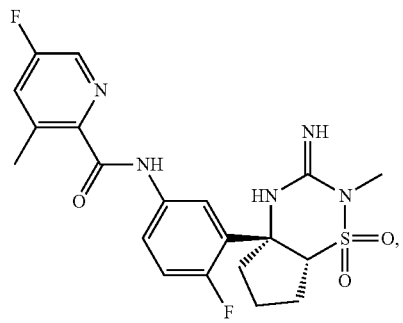
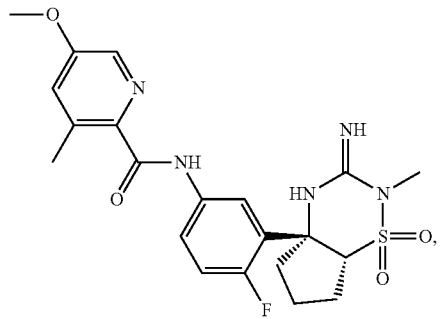 [SMILES: COc1cnc(C(=O)Nc2ccc(F)c([C@]34CCC[C@H]3S(=O)(=O)N(C)C(=N)N4)c2)c(C)c1]
-continued
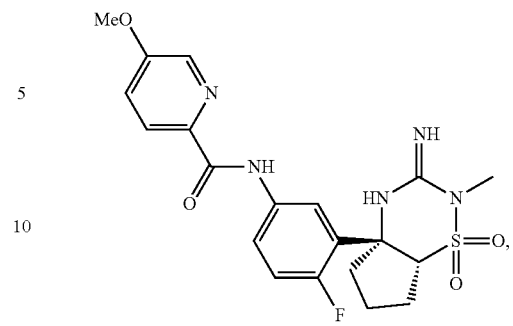
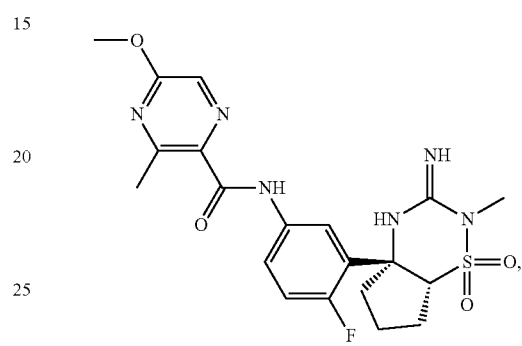
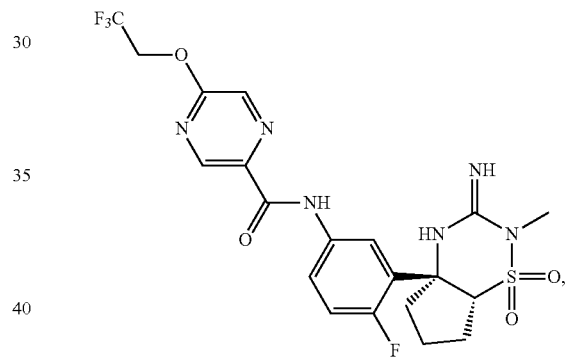
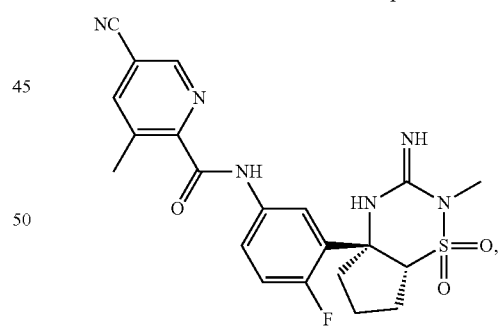
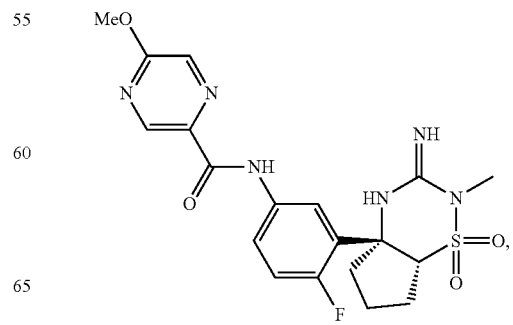

-continued
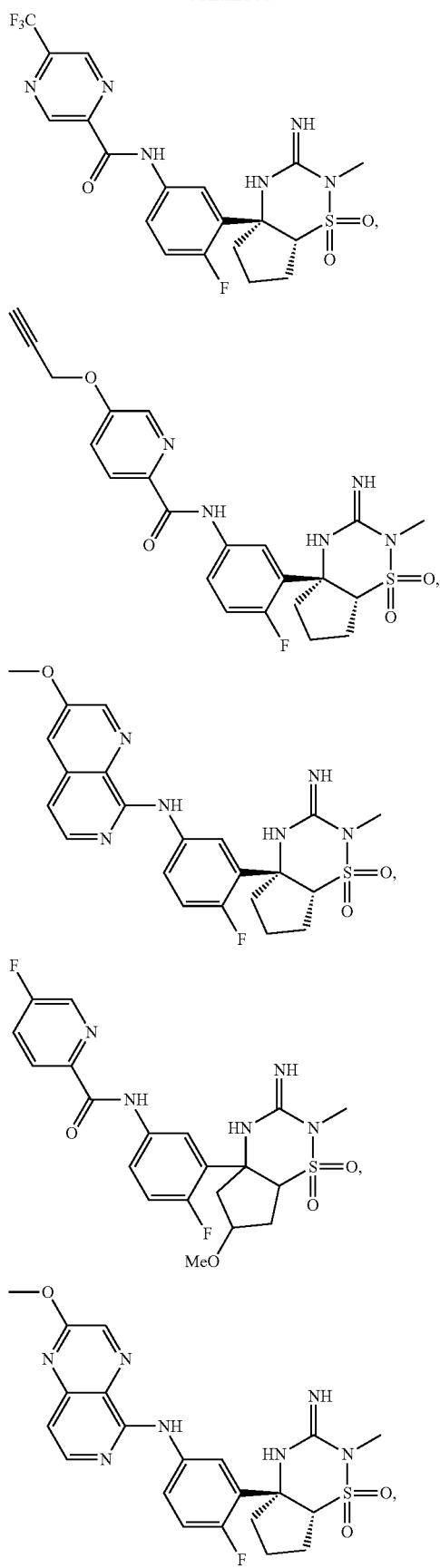
-continued
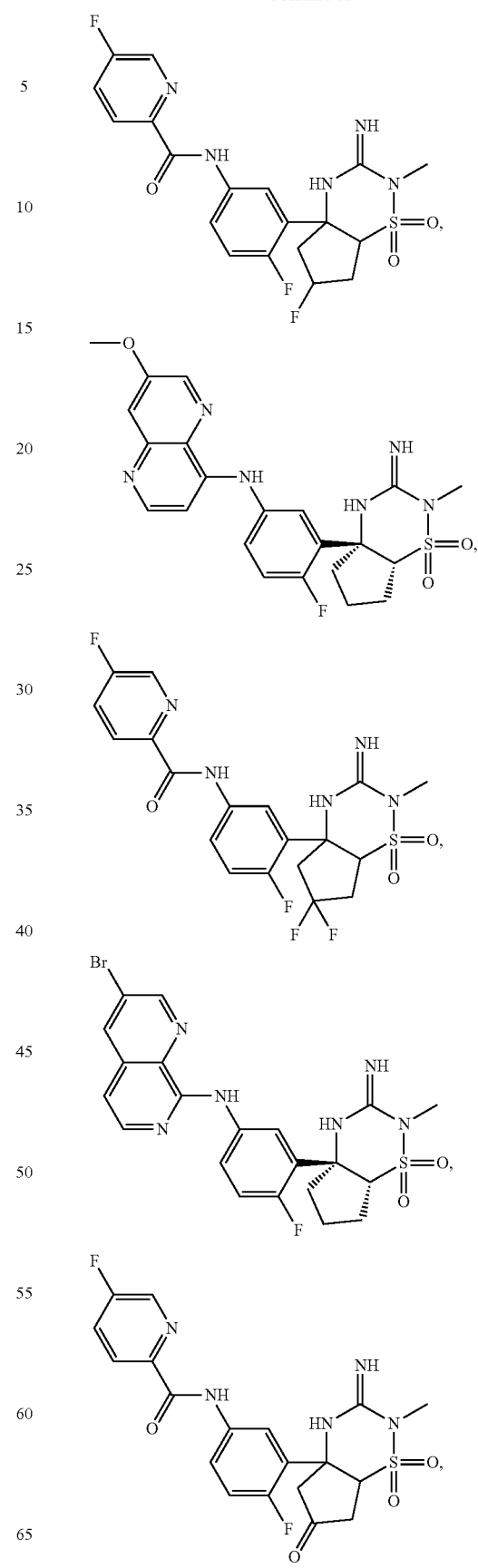

-continued
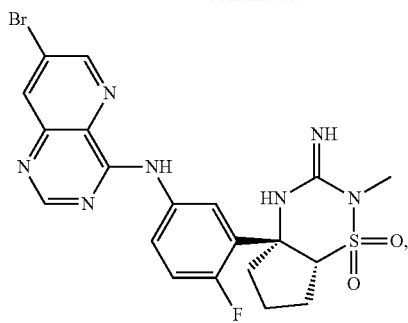
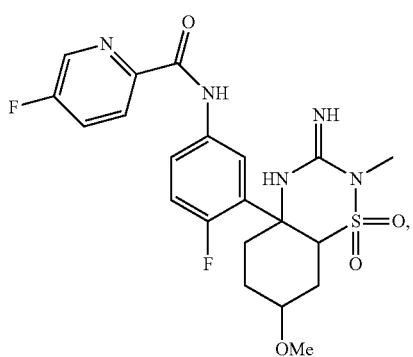
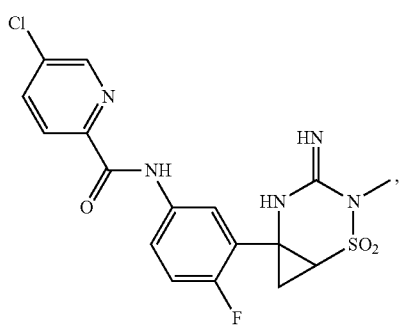
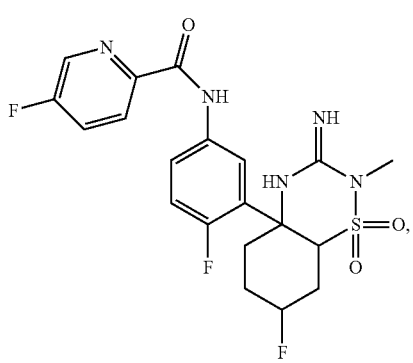
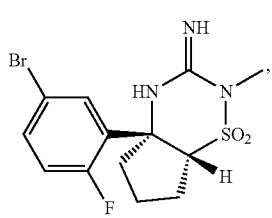
-continued
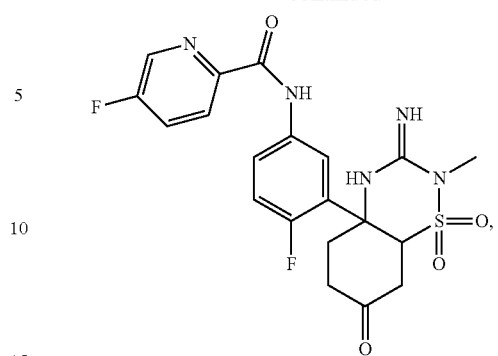
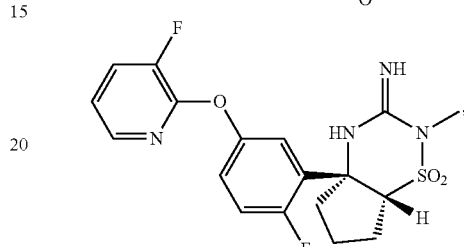
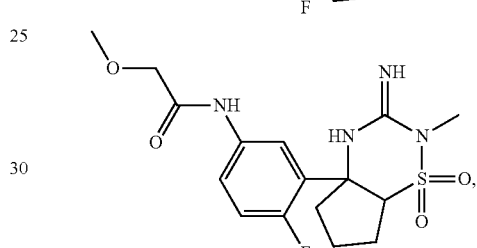
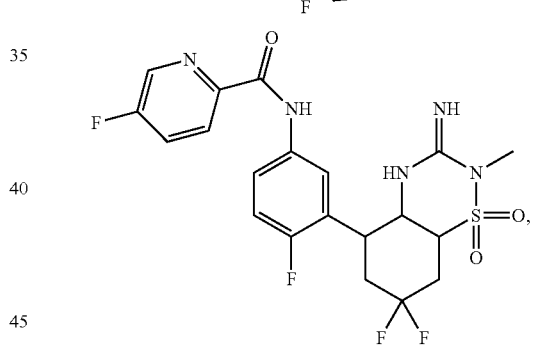
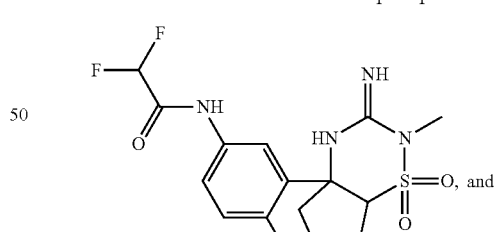
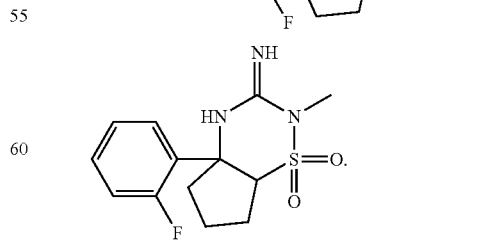
12. A pharmaceutical composition comprising a compound according to claim 1, or a tautomer thereof, or a pharmaceutically acceptable salt of said compound or said tautomer, and a pharmaceutically acceptable carrier or diluent.

13. A method of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease, said method comprising administering a compound according to claim 1, or a tautomer thereof, or a pharmaceutically acceptable salt of said compound or said tautomer, to a patient in need thereof in an amount effective to treat said disease or pathology.

14. The method of claim 13, wherein disease or pathology is Alzheimer's disease.

* * * * *